(12) United States Patent
Kim

(10) Patent No.: US 10,960,133 B2
(45) Date of Patent: Mar. 30, 2021

(54) INTERNAL PRESSURE-ADJUSTABLE LIQUID MEDICINE INJECTION APPARATUS

(71) Applicant: E-WHA MEDITECH INC., Goyang-si (KR)

(72) Inventor: Young Mu Kim, Gimpo-si (KR)

(73) Assignee: E-WHA MEDITECH INC., Goyang-si (KR)

( * ) Notice: Subject to any disclaimer, the term of this patent is extended or adjusted under 35 U.S.C. 154(b) by 219 days.

(21) Appl. No.: 16/090,476

(22) PCT Filed: Apr. 11, 2017

(86) PCT No.: PCT/KR2017/003912
§ 371 (c)(1),
(2) Date: Oct. 1, 2018

(87) PCT Pub. No.: WO2017/179887
PCT Pub. Date: Oct. 19, 2017

(65) Prior Publication Data
US 2019/0111205 A1  Apr. 18, 2019

(30) Foreign Application Priority Data

Apr. 15, 2016 (KR) .................. 10-2016-0045959
Nov. 1, 2016 (KR) .................. 10-2016-0144456

(51) Int. Cl.
*A61M 5/145* (2006.01)
*A61M 5/168* (2006.01)
(Continued)

(52) U.S. Cl.
CPC ...... *A61M 5/1452* (2013.01); *A61M 5/14526* (2013.01); *A61M 5/16881* (2013.01);
(Continued)

(58) Field of Classification Search
CPC combination set(s) only.
See application file for complete search history.

(56) References Cited

U.S. PATENT DOCUMENTS 6,142,181 A * 11/2000 Schumacher ....... F16K 11/0716
137/625.21
2005/0209562 A1 * 9/2005 Kim .................. A61M 5/14526
604/141
(Continued)

FOREIGN PATENT DOCUMENTS

JP    52152989 S    11/1977
JP    56141274 S    10/1981
(Continued)

OTHER PUBLICATIONS

European Extended Search Report for Corresponding International Application No. PCT/KR2017/003912 (8 Pages) (dated Oct. 22, 2019).
(Continued)

*Primary Examiner* — Bhisma Mehta
*Assistant Examiner* — Hamza A Darb
(74) *Attorney, Agent, or Firm* — Lucas & Mercanti, LLP

(57) ABSTRACT

A liquid medicine injection apparatus of the present invention is directed to improvement of a precise and detailed technology that can implement two functions of a high liquid medicine injection pressure and easy filling of the apparatus with a liquid medicine in a single apparatus without a separate additional unit, i.e., a technology for effectively adjusting an internal pressure of the apparatus depending on a liquid medicine filling mode and a liquid medicine injection mode. In the liquid medicine injection apparatus of the present invention, when an internal pressure of the apparatus exceeds a preset pressure due to a gas generated in a gas-generating unit of the apparatus, a switch member in the liquid medicine injection apparatus can
(Continued)

operate as a pressure regulating valve, thereby constantly keeping the internal pressure of the apparatus at the preset pressure.

22 Claims, 14 Drawing Sheets

(51) Int. Cl.
*A61M 5/315* (2006.01)
*A61M 5/142* (2006.01)

(52) U.S. Cl.
CPC .................. *A61M 5/31515* (2013.01); *A61M 2005/14204* (2013.01); *A61M 2205/3341* (2013.01); *A61M 2205/3372* (2013.01)

(56) References Cited

U.S. PATENT DOCUMENTS

| | | | |
|---|---|---|---|
| 2007/0224055 | A1 | 9/2007 | Anex et al. |
| 2008/0147007 | A1 | 6/2008 | Freyman |

FOREIGN PATENT DOCUMENTS

| | | |
|---|---|---|
| KR | 10-2003-0035701 A | 5/2003 |
| KR | 10-1697980 B1 | 1/2017 |
| WO | 2001089607 A2 | 11/2001 |
| WO | 2002011791 A1 | 2/2002 |
| WO | 2002055128 A2 | 7/2002 |

OTHER PUBLICATIONS

International Search Report for Corresponding International Application No. PCT/KR2017/003912 (2 Pages) (dated Aug. 3, 2017).

* cited by examiner

INTERNAL PRESSURE-ADJUSTABLE LIQUID MEDICINE INJECTION APPARATUS

CROSS-REFERENCE TO RELATED APPLICATIONS

This application is a 371 of PCT/KR2017/003912, filed Apr. 11, 2017 which claims the benefit of Korean Patent Application No. 10-2016-0045959, filed Apr. 15, 2016 and Korean Patent Application No. 10-2016-0144456, filed Nov. 1, 2016 the contents of each of which are incorporated herein by reference.

TECHNICAL FIELD

The present invention relates to an internal pressure-adjustable liquid medicine injection apparatus, and more particularly, to a liquid medicine injection apparatus wherein an internal pressure of the apparatus is to be in equilibrium with an external atmospheric pressure upon filling of the apparatus with a liquid medicine and a high pressure is applied to the inside of the apparatus upon injection of the liquid medicine into a patient's body, thereby facilitating the filling of the apparatus with the liquid medicine and further enabling the accommodated liquid medicine to be stably and continuously injected into the patient's body at a constant flow rate while being less influenced by changes in an environment such as an elevation of the apparatus, an external temperature or the like.

Specifically, the present invention relates to a liquid medicine injection apparatus, wherein upon filling of the apparatus with a liquid medicine, a switch member is not operated so that the inside of the apparatus is in communication with an external atmosphere so as to allow resistance to inflow of the liquid medicine, caused by an injection piston, upon filling of the apparatus with the liquid medicine to be reduced, thereby facilitating the filling of the apparatus with the liquid medicine, and upon injection of the liquid medicine into the patient's body, the switch member is operated with a propulsive force of a gas generated in a gas-generating unit of the apparatus so as to block communication between the inside of the apparatus and the external atmosphere while allowing a high pressure caused by the generated gas to be exerted on the injection piston, thereby enabling the accommodated liquid medicine to be stably and continuously injected into the patient's body at a constant flow rate while being less influenced by changes in an environment such as an elevation of the apparatus, an external temperature or the like.

In addition, the present invention relates to an internal pressure-adjustable liquid medicine injection apparatus, wherein when an internal pressure of the apparatus exceeds a preset pressure due to a gas generated in a gas-generating unit of the apparatus, a switch member can function as a pressure regulating valve, thereby constantly keeping the internal pressure of the apparatus at the preset pressure.

BACKGROUND ART

When a liquid medicine of special injectable drugs such as anticancer drugs and antibiotics is injected into a patient's body, a constant amount of liquid medicine should be continuously injected for a considerably long period of time depending on a patient's condition. If the special injectable drugs are not injected continuously and consistently to meet an amount required by a patient, there is concern that a shock occurs, leading to a medical accident. In view of such a problem, there has been devised and used a mechanical apparatus for injecting a predetermined amount of liquid medicine per unit time into a patient's body.

However, such a conventional mechanical apparatus is an apparatus in which a plunger of a syringe is gradually pushed by a driving force of a motor and an auxiliary unit such as a motor is required so that the apparatus may be larger in size and unsuitable for being carried by a patient.

In view of such a problem, Korean Patent No. 10-0262930 discloses a liquid medicine injection apparatus that can be carried by a patient. This conventional portable liquid medicine injection apparatus has a configuration in which an elastic pouch (also referred to as "balloon") made of a rubber material is provided within a chamber of the apparatus. The elastic balloon has an inlet and an outlet. When the liquid medicine is introduced into the pouch through the inlet, the pouch is swelled. The pouch is configured such that the liquid medicine may be slowly discharged through the outlet mounted with an elongated tube. The liquid medicine is discharged at a small flow rate and injected into a patient's vein.

In the liquid medicine injection apparatus having such an elastic balloon, however, a defective product having a non-uniform thickness or with a minute hole generated therein may be produced when the balloon is manufactured. These defects change elasticity so that the pouch may not have desired elasticity. Then, it is difficult to constantly keep an amount of injection per unit time. Moreover, the elastic balloon may have elasticity that varies depending on the amount of the liquid medicine remaining therein, and thus an external force (elastic restoring force) that influences a flow of the liquid medicine may be different at initial and end stages of the injection.

In addition, the liquid medicine injection apparatus provided with the elastic balloon has a weak physical force for pushing the liquid medicine. The liquid medicine injection apparatus provided with the elastic balloon having a low liquid medicine injection pressure is very sensitive to external environments such as an elevation of the apparatus, a temperature and the like, and thus a flow rate of the liquid medicine to be injected into the patient's body is extremely changed. In particular, when the flow rate of the liquid medicine to be injected into the patient's body is large, the liquid medicine may not be constantly pushed if the liquid medicine injection pressure is low. For this reason, it is necessary to increase the liquid medicine injection pressure in the liquid medicine injection apparatus. Furthermore, a higher pressure is required if the flow rate is intended to be changed from time to time during injection of the liquid medicine into the patient's body.

In order to overcome such a problem, a gas-generating type liquid medicine injection apparatus disclosed in Korean Patent No. 10-0507593 has been known. In this apparatus, an injection piston in a cylinder of the apparatus is steadily and slowly moved forward by a high pressure of a generated gas, and a liquid medicine accommodated within a liquid medicine storage space in the cylinder is steadily and constantly injected into a patient's body at a constant flow rate by the forward movement of the injection piston.

However, in the gas-generating type liquid medicine injection apparatus, there is a problem that if the liquid medicine injection pressure is increased, resistance to inflow of the liquid medicine is generated at a stage of filling the liquid medicine storage space with the liquid medicine so that it is difficult to fill the liquid medicine storage space with the liquid medicine. For this reason, the conventional gas-generating type liquid medicine injection apparatus has a limitation on an increase of the liquid medicine injection pressure for facilitating the filling of the liquid medicine storage space with the liquid medicine.

In other words, the conventional gas-generating type liquid medicine injection apparatus as described above is an excellent technology, although it can be continuously improved similarly to other excellent technologies. For example, there is a need to provide a novel gas-generating type liquid medicine injection apparatus that can simultaneously address requirements for an increase in the liquid medicine injection pressure so as to stably and continuously inject the liquid medicine into the patient's body while being less affected by changes in the environment such as an elevation of the apparatus or an external temperature, and a challenge of filling the liquid medicine storage space with the liquid medicine at a high liquid medicine injection pressure.

Accordingly, the liquid medicine injection apparatus of the present invention is directed to improvement of a precise and detailed technology that can implement two functions of the high liquid medicine injection pressure and easy filling of the apparatus with the liquid medicine in a single apparatus without a separate additional unit, i.e., a technology for effectively adjusting the internal pressure of the apparatus depending on a liquid medicine filling mode and a liquid medicine injection mode.

SUMMARY OF THE INVENTION

An object of the present invention is to provide a liquid medicine injection apparatus capable of adjusting an internal pressure thereof according to a liquid medicine filling mode and a liquid medicine injection mode, wherein the internal pressure of the apparatus is to be in equilibrium with an external atmospheric pressure upon filling of the apparatus with a liquid medicine and a high pressure is applied to the inside of the apparatus upon injection of the liquid medicine into a patient's body, thereby facilitating the filling of the apparatus with the liquid medicine and further enabling the accommodated liquid medicine to be stably and continuously injected into the patient's body at a constant flow rate while being less influenced by changes in an environment such as an elevation of the apparatus, an external temperature or the like.

Specifically, an object of the present invention is to provide a liquid medicine injection apparatus, wherein upon filling of the apparatus with a liquid medicine, a switch member is not operated so that the inside of the apparatus is in communication with an external atmosphere so as to allow resistance to inflow of the liquid medicine, caused by an injection piston, upon filling of the apparatus with the liquid medicine to be reduced, thereby facilitating the filling of the apparatus with the liquid medicine, and upon injection of the liquid medicine into the patient's body, the switch member is operated with a propulsive force of a gas generated in a gas-generating unit of the apparatus so as to block communication between the inside of the apparatus and the external atmosphere while allowing a high pressure caused by the generated gas to be exerted on the injection piston, thereby enabling the accommodated liquid medicine to be stably and continuously injected into the patient's body at a constant flow rate while being less influenced by changes in an environment such as an elevation of the apparatus, an external temperature or the like.

In addition, an object of the present invention is to provide an internal pressure-adjustable liquid medicine injection apparatus, wherein when an internal pressure of the apparatus exceeds a preset pressure due to a gas generated in a gas-generating unit of the apparatus, a switch member can function as a pressure regulating valve, thereby constantly keeping the internal pressure of the apparatus at the preset pressure.

As for the aforementioned gas-generating type liquid medicine injection apparatus in the art to which the present invention pertains, an operation of filling a liquid medicine storage space in a cylinder with a liquid medicine should be performed prior to use of the apparatus. However, there is a problem of difficulty in filling the liquid medicine storage space with the liquid medicine if a liquid medicine injection pressure is increased to stably and continuously inject the liquid medicine into a patient's body while being less influenced by changes in an environment such as an elevation of the liquid medicine injection apparatus, an external temperature or the like. Accordingly, the present invention provides a precise and detailed technology which can stably and continuously inject the liquid medicine into the patient's body while being less influenced by changes in an environment such as an elevation of the liquid medicine injection apparatus, an external temperature or the like and can communicate the inside of the apparatus with an external atmosphere to equilibrate the internal pressure of the apparatus to an atmospheric pressure when the liquid medicine storage space is filled with the liquid medicine, thereby facilitating the filling of the liquid medicine storage space with the liquid medicine, in order to solve the problem of difficulty in filling the liquid medicine storage with the liquid medicine at a high liquid medicine injection pressure.

An internal pressure-adjustable liquid medicine injection apparatus according to one embodiment of the present invention for achieving the objects includes:

a cylinder elongated in one direction and having one end with a liquid medicine-flowing tube connected thereto and the other end with a gas-generating unit coupled thereto, wherein a liquid medicine flows into and out of the cylinder through the liquid medicine-flowing tube and the gas-generating unit has a gas-generating space in which a gas is generated;

an injection piston hermetically movable in the cylinder and dividing an internal space of the cylinder into a liquid medicine storage space and a gas-supplied space, wherein the liquid medicine flows through the liquid medicine-flowing tube and fills the liquid medicine storage space and the gas generated in the gas-generating unit is supplied to the gas-supplied space; and a switch member provided between the gas-supplied space and the gas-generating space to connect the gas-supplied space to an atmosphere upon filling of the liquid medicine storage space with the liquid medicine and to connect the gas-supplied space to the gas-generating space upon injection of the liquid medicine.

The switch member may include a switch cylinder connected to the atmosphere, the gas-supplied space and the gas-generating space; and a switch piston movably installed in the switch cylinder to connect the gas-supplied space to the atmosphere or connect the gas-supplied space to the gas-generating space depending on a location of the switch piston within the switch cylinder.

The switch cylinder may include a first hole connecting the atmosphere to the inside of the switch cylinder; a second hole connecting the gas-generating space and the inside of the switch cylinder; and a third hole connecting the gas-supplied space and the inside of the switch cylinder and positioned between the first hole and the second hole.

For example, upon filling of the liquid medicine storage space with the liquid medicine, the switch piston may be positioned between the third hole and the second hole in the switch cylinder to connect the gas-supplied space to the atmosphere, and upon injection of the liquid medicine, the switch piston may be positioned between the third hole and the first hole in the switch cylinder to connect the gas-supplied space and the gas-generating space. The switch cylinder may further include a fourth hole exposed to an outside and the switch member may further include a plug for blocking the fourth hole. It is preferable that the plug is made of a light-transmitting material so that a user may visually recognize a movement of the switch piston to understand whether the switch member is normally operated. For example, the plug may be made of a transparent material or a translucent material.

Upon injection of the liquid medicine, if the internal pressure of the gas-supplied space exceeds a preset pressure value, the switch member may form a bypass flow passage for connecting the gas-supplied space to the atmosphere and discharge an amount of gas corresponding to an excess pressure to an outside through the bypass flow passage.

The switch member may include a switch cylinder connected to the atmosphere, the gas-supplied space and the gas-generating space and comprising a bypass flow passage for connecting the gas-supplied space to the atmosphere; a switch piston movably installed in the switch cylinder to connect the gas-supplied space to the atmosphere or connect the gas-supplied space to the gas-generating space depending on a location of the switch piston within the switch cylinder; and a switch elastic member provided in the switch cylinder, positioned between the atmosphere and the switch piston and capable of exerting an elastic force on the switch piston so as to close the bypass flow passage before the internal pressure of the gas-supplied space exceeds a preset pressure value during the injection of the liquid medicine.

The switch cylinder may include a first hole connecting the atmosphere to the inside of the switch cylinder; a second hole connecting the gas-generating space and the inside of the switch cylinder; a third hole connecting the gas-supplied space and the inside of the switch cylinder and positioned between the first hole and the second hole; and a stepped portion formed between the first hole and the third hole and forming the bypass flow passage connected to the first hole.

For example, upon filling of the liquid medicine storage space with the liquid medicine, the switch piston may be positioned between the third hole and the second hole in the switch cylinder to connect the gas-supplied space to the atmosphere, and upon injection of the liquid medicine, the switch piston may be positioned between the third hole and the stepped portion in the switch cylinder to connect the gas-supplied space to the gas-generating space; and if the internal pressure of the gas-supplied space exceeds a preset pressure value during the injection of the liquid medicine, the switch piston may be positioned between the first hole and the stepped portion in the switch cylinder to open the bypass flow passage for connecting the gas-supplied space to the atmosphere.

A distance from the first hole to the stepped portion may be smaller than a length of the switch elastic member or smaller than the sum of the length of the switch elastic member and a length of the switch piston. The switch cylinder may be formed integrally with the body part of the gas-generating unit.

An internal pressure-adjustable liquid medicine injection apparatus according to another embodiment of the present invention for achieving the objects includes:

a cylinder having one end with a liquid medicine-flowing tube connected thereto and the other end with a gas-generating unit coupled thereto, wherein the other end is opposite to the liquid medicine-flowing tube and the gas-generating unit generates a gas;

an injection piston hermetically movable in the cylinder and dividing an internal space of the cylinder into a liquid medicine storage space and a gas-supplied space, wherein the liquid medicine flows through the liquid medicine-flowing tube and fills the liquid medicine storage space and the gas generated in the gas-generating unit is supplied to the gas-supplied space; and a switch member installed in the gas-generating unit to face toward the inside of the gas-supplied space, wherein the switch member has an internal connection passage for connecting an external air entrance formed at one side of the body part of the gas-generating unit to the gas-supplied space, and a shut-off valve, the shut-off valve being hermetically moveable in the internal connection passage and dividing the internal connection passage into an external air inflow space into which external air can flow from the external air entrance and a generated-gas inflow space into which the gas from the gas-generating unit flows, when the liquid medicine storage space is filled with the liquid medicine prior to the generation of the gas in the gas-generating unit, the shut-off valve is positioned at a location where external air from the external air entrance is caused to flow into the external air inflow space and the external air inflow space is in communication with the gas-supplied space, thereby equilibrating the internal pressure of the gas-supplied space to an atmospheric pressure, and when the liquid medicine is injected after the gas is generated in the gas-generating unit, the gas generated in the gas-generating unit flows into the generated-gas inflow space to move the shut-off valve toward the external air inflow space, thereby blocking inflow of the external air from the external air entrance into the external air inflow space so that a pressure of the gas generated by the gas-generating unit is exerted on the injection piston in the gas-supplied space.

Moreover, in the internal pressure-adjustable liquid medicine injection apparatus according to the other embodiment of the present invention, the shut-off valve may have a front end facing the external air inflow space, and a body part hermetically movable along a guide wall of the internal connection passage, and may be formed with a through passage extending a through hole of the front end to a through hole formed in a side surface of the body part. The guide wall of the internal connection passage may be formed with a through hole for communicating the internal connection passage with the gas-supplied space.

When the liquid medicine storage space is filled with the liquid medicine prior to the generation of the gas in the gas-generating unit, the through hole formed in the side surface of the body part of the shut-off valve may be placed a location where it is aligned with the through hole of the internal connection passage, and the external air flowing from the external air entrance into the external air inflow space may flow through the through hole of the front end, the through passage and the through hole formed in the side surface of the body part and then flow into the gas-supplied space via the through hole of the internal connection passage which is aligned with the through hole formed in the side surface of the body part.

Furthermore, in the internal pressure-adjustable liquid medicine injection apparatus according to the other embodiment of the present invention, an end of the external air inflow space of the internal connection passage may be opened, and the apparatus may further include a sealing member to seal this opened end. The sealing member may include a stepped sealing cap and a rubber packing member fitted into and coupled with a concave receiving portion of the sealing cap, a stepped portion of the sealing cap may be inserted into and tightly coupled with the opened end, and the rubber packing member may face the external air inflow space.

When the liquid medicine is injected after the gas is generated in the gas-generating unit, the gas generated in the gas-generating unit flows into the generated-gas inflow space through a gas-flowing passage for connecting the gas-generating unit to the generated-gas inflow space, so as to push a rear portion of the body part of the shut-off valve; and the shut-off valve is moved toward the external air inflow space so that the front end of the shut-off valve is brought into contact with the sealing member. Accordingly, the external air from the external air entrance is prevented from flowing via the through hole of the front end of the shut-off valve.

In particular, when the front end of the shut-off valve presses against and is brought into contact with the rubber packing member constituting the sealing member, the front end of the shut-off valve is in close contact with and blocked by the rubber packing member, so that it is possible to securely prevent the external air from leaking to the through hole formed at the front end of the shut-off valve. Accordingly, a high pressure of the gas generated by the gas-generating unit is exerted on the injection piston in the gas-supplied space, so that the injection piston can be effectively moved forward and it is possible to stably and continuously inject the liquid medicine filled in the liquid medicine storage space into the patient's body at a constant flow rate.

Further, in the internal pressure-adjustable liquid medicine injection apparatus according to the other embodiment of the present invention, a plurality of ring-shaped protrusions, preferably at least two, more preferably four ring-shaped protrusions may be formed on a circumference of the body part of the shut-off valve. However, the present invention is not limited thereto, and it will be apparent that various numbers of ring-shaped protrusions may be formed.

At least one of the ring-shaped protrusions may be in close contact with at least one stepped portion formed on the guide wall of the internal connection passage. In this state, before the gas generated in the gas-generating unit is introduced into the generated-gas inflow space, the through hole formed in the side surface of the body part of the shut-off valve is securely aligned with the through hole of the internal connection passage. Meanwhile, when the gas generated in the gas-generating unit is introduced into the generated-gas inflow space, the pressure of the introduced gas is exerted on a rear portion of the body part of the shut-off valve so that the shut-off valve may overcome an obstacle to a movement, which is caused by engagement of the ring-shaped protrusion with the stepped portion, and be moved toward the external air inflow space.

With the aforementioned configuration, it is possible to prevent the shut-off valve from being moved due to temporary external impact or external air, so that the internal pressure of the gas-supplied space is stably equilibrated to the atmospheric pressure before the gas is generated in the gas-generating unit, whereas upon generation of the gas in the gas-generating unit, the gas pressure generated in response to a liquid medicine injection mode enables the shut-off valve to overcome an obstacle to a movement, which is caused by the stepped portion, and to be moved toward the external air inflow space, and the front end of the shut-off valve is in close contact with the sealing member to block the inflow of external air.

Moreover, in the internal pressure-adjustable liquid medicine injection apparatus according to the other embodiment of the present invention, a sealing ring may be inserted between and coupled to the ring-shaped protrusions. The sealing ring allows the shut-off valve to be hermetically movable along the guide wall of the internal connection passage.

Additionally, in the internal pressure-adjustable liquid medicine injection apparatus according to the other embodiment of the present invention, the apparatus may further include a tension spring fixedly provided in the generated-gas inflow space and coupled with the body part of the shut-off valve. The tension spring and the shut-off valve may be housed in the internal connection passage through the opened end of the external air inflow space as described above.

When the gas is generated in the gas-generating unit, the gas pressure generated in response to the liquid medicine injection mode enables the shut-off valve to overcome the elastic restoring force caused by the tension spring and to be moved toward the external air inflow space, and the front end of the shut-off valve is in close contact with the sealing member to block the inflow of external air. Meanwhile, the tension spring prevents the shut-off valve from being moved due to temporary external impact or external air by means of the elastic restoring force, thereby assisting in attaining a stable equilibrium between the internal pressure of the gas-supplied space and the atmospheric pressure before the gas is generated in the gas-generating unit. In addition, when the generation of the gas is completed, the elastic restoring force of the tension spring helps to return the shut-off valve to its original state where the injection of the liquid medicine is not initiated.

Furthermore, in the internal pressure-adjustable liquid medicine injection apparatus according to the other embodiment of the present invention, a gas-permeable/liquid-impermeable hydrophobic filter may be provided at the external air entrance. Such hydrophobic filter allows the external air to flow into the apparatus through the external air entrance, but prevents water, the liquid medicine, a liquid contaminant and the like from flowing into the apparatus from the outside.

Meanwhile, most of the elements constituting the internal pressure-adjustable liquid medicine injection apparatus according to the other embodiment of the present invention may be formed of a material suitable for withstanding external impact and may be formed of a plastic material, a synthetic resin or the like that have been well known in the art. The sealing rings and the rubber packing member may be formed of a known elastic rubber material. Furthermore, plastic or spring steel may be used as a material for the tension spring. However, it will be readily understood by those skilled in the art that the present invention is not limited thereto and the aforementioned elements may be formed of various materials well known in the art, wherein the materials meet the object of the present invention, satisfy biocompatibility, are less corroded and have predetermined durability.

Advantageous Effects

The liquid medicine injection apparatus according to the present invention has an advantage of adjustability of the internal pressure of the apparatus depending on the liquid medicine filling mode and the liquid medicine injection mode, wherein the internal pressure of the apparatus is to be in equilibrium with an external atmospheric pressure upon filling of the apparatus with the liquid medicine and a high pressure is applied to the inside of the apparatus upon injection of the liquid medicine into a patient's body, thereby facilitating the filling of the apparatus with the liquid medicine and further enabling the accommodated liquid medicine to be stably and continuously injected into the patient's body at a constant flow rate while being less influenced by changes in an environment such as an elevation of the apparatus, an external temperature or the like.

Specifically, the liquid medicine injection apparatus according to the present invention is advantageous in that upon filling of the apparatus with the liquid medicine, the switch member is not operated so that the inside of the apparatus is in communication with an external atmosphere so as to allow resistance to inflow of the liquid medicine, caused by the injection piston, upon filling of the apparatus with the liquid medicine to be reduced, thereby facilitating the filling of the apparatus with the liquid medicine, and upon injection of the liquid medicine into the patient's body, the switch member is operated with the propulsive force of the gas generated in the gas-generating unit of the apparatus so as to block communication between the inside of the apparatus and the external atmosphere while allowing a high pressure caused by the generated gas to be exerted on the injection piston, thereby enabling the accommodated liquid medicine to be stably and continuously injected into the patient's body at a constant flow rate while being less influenced by changes in an environment such as an elevation of the apparatus, an external temperature or the like.

In addition, the liquid medicine injection apparatus according to the present invention is further advantageous in that when the internal pressure of the apparatus exceeds a preset pressure due to the gas generated in the gas-generating unit of the apparatus, the switch member can function as a pressure regulating valve, thereby constantly keeping the internal pressure of the apparatus at the preset pressure.

BRIEF DESCRIPTION OF DRAWINGS

These and other features of the present invention will be apparent to those skilled in the art from the following descriptions of embodiments of the present invention made with reference to accompanying drawings, in which.

DETAILED DESCRIPTION OF THE INVENTION

Hereinafter, preferred embodiments according to the present invention will be described in detail with reference to the accompanying drawings. The following embodiments of the present invention are just to implement the present invention and are not intended to limit or restrict the scope of the present invention. Thus, those that can be easily contemplated by persons skilled in the art from the detailed description and examples of the present invention are interpreted to fall within the scope of the present invention. References cited herein are incorporated herein by reference.

Figure 1:
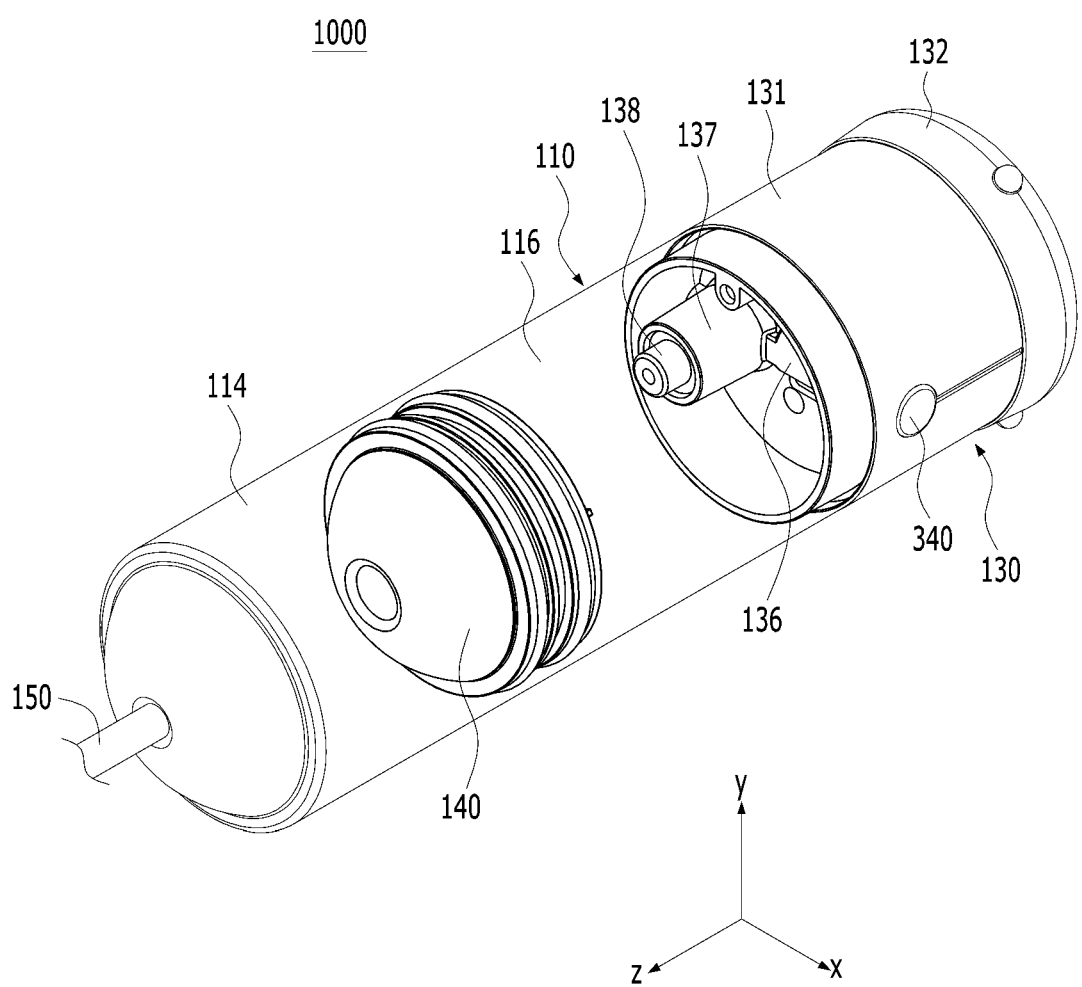
FIG. 1 is a perspective view schematically illustrating an internal pressure-adjustable liquid medicine injection apparatus 1000 according to a first embodiment of the present invention.
Figure 2:
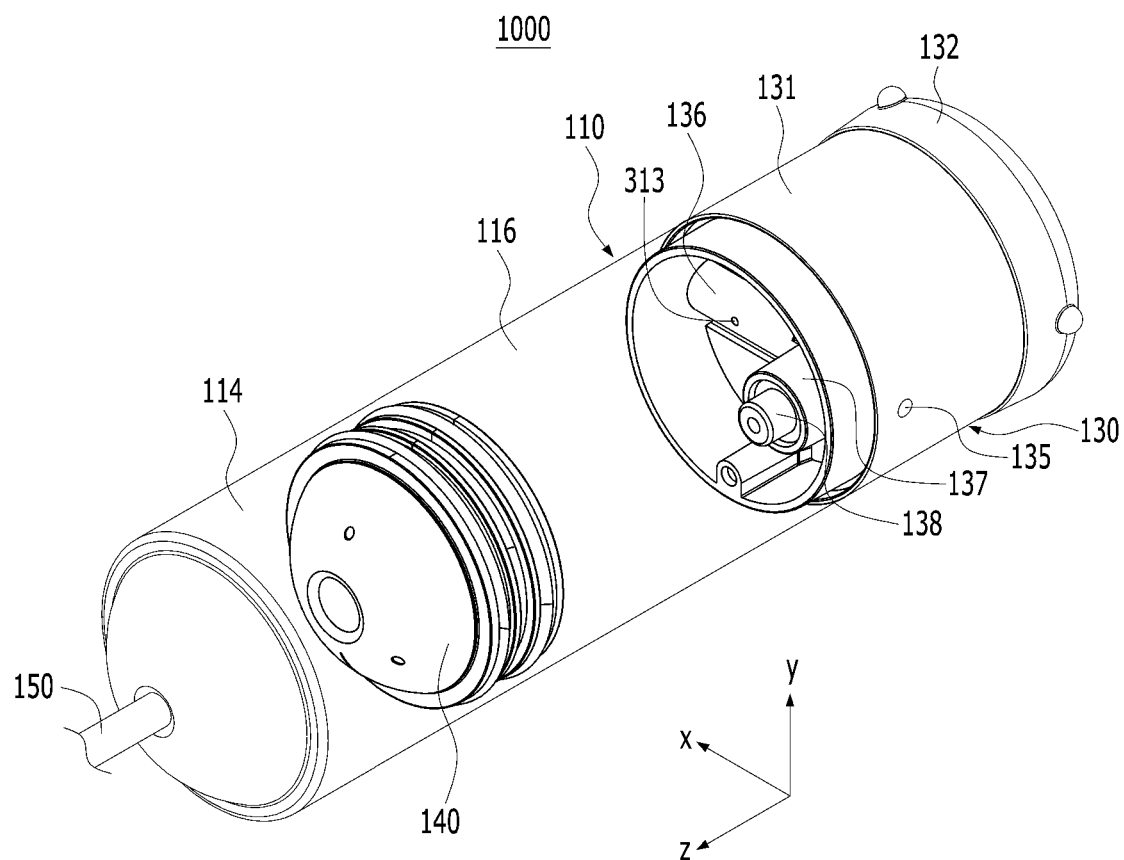
FIG. 2 is a perspective view schematically illustrating the internal pressure-adjustable liquid medicine injection apparatus 1000 according to the first embodiment of the present invention when viewed in another direction.
Figure 3:
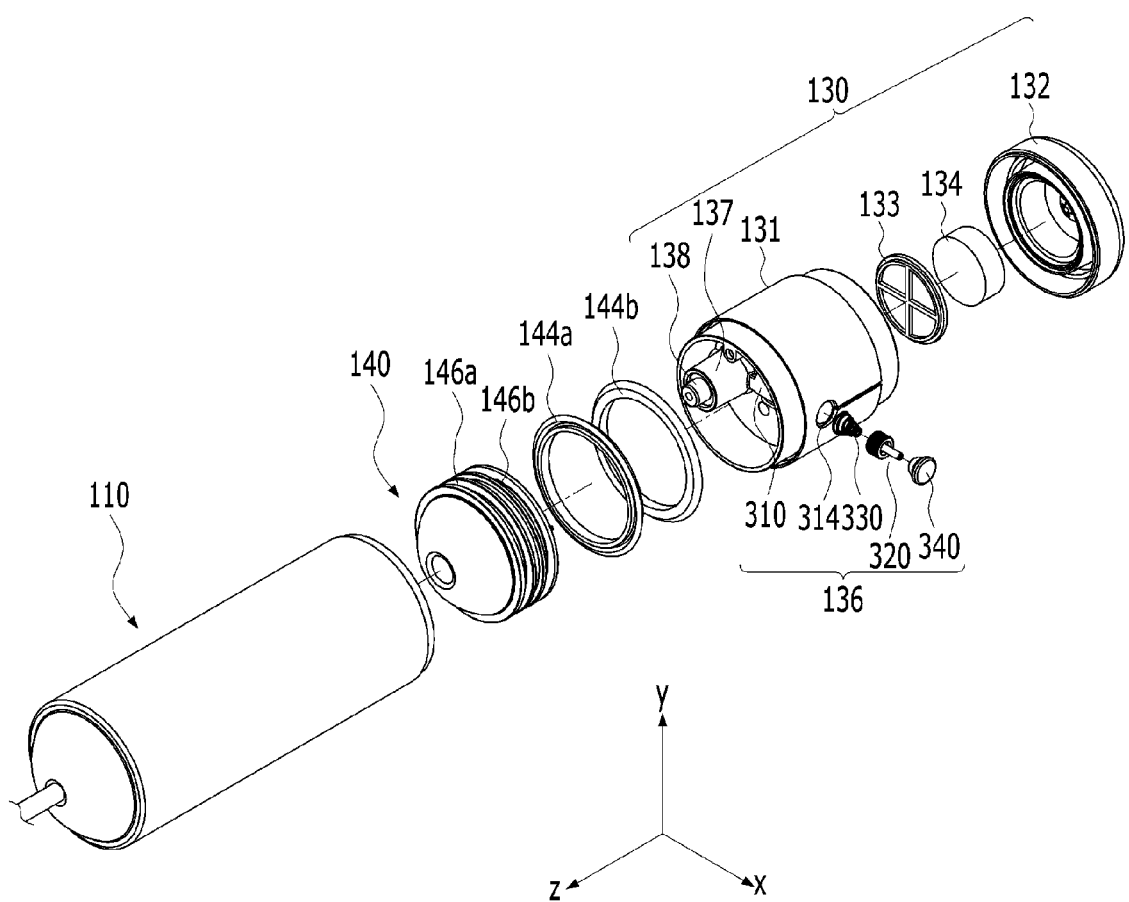
FIG. 3 is an exploded perspective view schematically illustrating a disassembled state of the internal pressure-adjustable liquid medicine injection apparatus 1000 according to the first embodiment of the present invention.

FIG. 1 is a perspective view schematically illustrating a liquid medicine injection apparatus 1000 according to a first embodiment of the present invention, and FIG. 2 is a perspective view schematically illustrating the liquid medicine injection apparatus 1000 according to the first embodiment of the present invention when viewed in another direction. FIG. 3 is an exploded perspective view of the liquid medicine injection apparatus 1000 according to the first embodiment of the present invention.

The internal pressure-adjustable liquid medicine injection apparatus 1000 according to the first embodiment of the present invention includes a generally cylindrical cylinder 110, an injection piston 140 and a switch member 136 as main components.

As shown in FIG. 1, a liquid medicine-flowing tube 150 through which the liquid medicine flows into and out of the cylinder is connected to one end of the generally cylindrical cylinder 110, and a gas-generating unit 130 is coupled to the other end of the cylinder.

The injection piston 140 is hermetically movable inside the cylinder 110 and divides an internal space of the cylinder 110 into a liquid medicine storage space 114 which the liquid medicine flows into through the liquid medicine-flowing tube 150 and fills, and a gas-supplied space 116 to which a gas generated in the gas-generating unit 130 is supplied. An end cap (not shown) may be provided at a distal end of the liquid medicine-flowing tube 150, and an injection needle or a catheter (not shown) may be connected to the end cap.

As shown in FIG. 3, sealing ring insertion grooves 146a and 146b are formed between ring-shaped protrusions on a circumference of the injection piston 140, and sealing rings 144a and 144b are fitted into and coupled to the sealing ring insertion grooves 146a and 146b, respectively. The injection piston 140 can be hermetically moved within the cylinder 110 by these sealing rings 144a and 144b.

As shown in FIGS. 1 to 3, the gas-generating unit 130 is largely composed of a body part 131 and a cap part 132. At this time, the body part 131 includes a gas-generating space 139 formed therein (see FIG. 6).

The gas-generating unit 130 accommodates a liquid material L and a solid material 134, wherein the liquid material L is accommodated in the body part 131 and the solid material is accommodated in the cap part 132. The solid material 134 is separated from the liquid material L by a partition wall 133 and is accommodated in the cap part 132. The solid material 134 may be pellets including sodium carbonate ($Na_2CO_3$) as a main component and the liquid material L may be an acidic liquid material such as citric acid that generates carbon dioxide upon reaction thereof with the solid material 134.

The liquid material L is accommodated by a gas permeable/liquid impermeable filter (not shown) provided on a circumference and a bottom of the body part 131, and the liquid material L does not flow into the gas-supplied space 116 of the cylinder 110 due to a liquid sealing function of this filter.

When the partition wall 133 is detached due to an external force exerted on the cap part 132 and the solid material 134 falls into the gas-generating space 139 in the body part 131, the solid material reacts with the liquid material L to generate a gas, i.e., carbon dioxide.

The generated gas passes through the gas permeable/liquid impermeable filter in the body part 131 and is discharged into the gas-supplied space 116 of the cylinder 110, thereby pushing a rear portion of the injection piston 140.

A boss 137 protruding from the body part 131 of the gas-generating unit 130 may be provided with a pressure regulating valve 138 for preventing the pressure of the gas from exceeding a pre-set pressure.

In order to prevent the liquid medicine from being injected into a patient's body at a flow rate higher than a preset flow rate, if a pressure in the gas-supplied space 116 becomes higher than the pre-set pressure, the pressure regulating valve 138 connects the gas-supplied space 116 to an outside (for example, the atmosphere) so as to discharge the gas in the gas-supplied space 116 to the outside. As a result, the pressure in the gas-supplied space 116 is kept constant.

Figure 10:
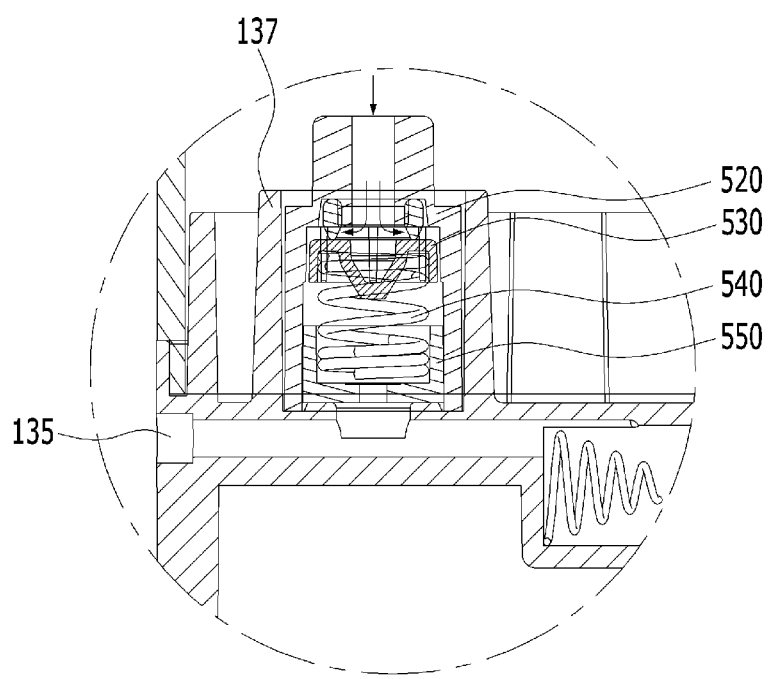
FIGS. 10 and 11 are views illustrating states before and after the operation of the pressure regulating valve, respectively.
Figure 11:
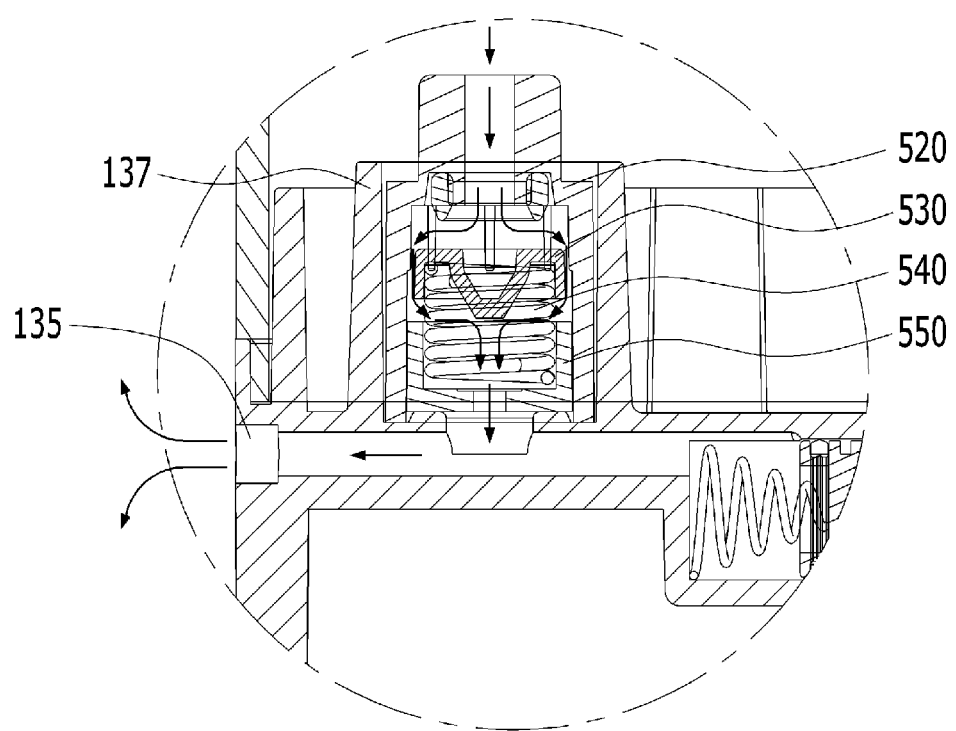

The pressure regulating valve 138 is explained with reference to FIGS. 6, 10 and 11. The pressure regulating valve 138 includes a generally cylindrical body part 520, an opening/closing member 530, an elastic member 540, a cap part 550 and the like.

The body part 520 of the pressure regulating valve has a generally cylindrical shape and can be coupled to an inner surface of the boss 137 in a fitting manner as shown in these figures. However, the present invention is not limited thereto. For example, the body part 520 of the pressure regulating valve may be installed in the boss 137 by various methods such as ultrasonic welding.

The body part 520 of the pressure regulating valve is installed at the boss 137 so as to protrude into the gas-supplied space 116. The protruding portion of the body part 520 is formed with an internal passage for allowing the gas to flow thereinto and pass therethrough. The opening/closing member 530 of the pressure regulating valve is installed to be exposed to the gas-supplied space 116 through the internal passage of the protruding portion so that the opening/closing member may be moved according to the pressure in the gas-supplied space 116.

The cap part 550 of the pressure regulating valve is installed within the body part 520 of the pressure regulating valve and on a side opposite to the opening/closing member 530. An opening is formed at a central portion of the cap part 550 to allow air to escape therefrom. At this time, the opening of the cap part 550 is in communication with the outside of the liquid medicine injection apparatus. More specifically, the opening of the cap part 550 is in communication with an external air entrance 135 formed in the body part 131 of the gas-generating unit 130.

The elastic member 540 of the pressure regulating valve is a coil spring and is provided between the opening/closing member 530 and the cap part 550. The elastic member 540 is retracted and compressed when the pressure in the gas-supplied space 116 becomes higher than the pre-set pressure.

When the pressure in the gas-supplied space 116 exceeds an internal pressure reference value (the pre-set pressure value), the gas in the gas-supplied space 116 overcomes an elastic restoring force of the elastic member 540 and then pushes the opening/closing member 530. At this time, a front surface of the opening/closing member 530, which has been in contact with an inner surface of the body part 520 (or a sealing ring provided on the inner surface of the body part) to block gas inflow, is spaced apart from the inner surface of the body part 520. Accordingly, the gas that has entered along the internal passage formed in the protruding portion of the body part 520 flows through a space between the front surface of the opening/closing member 530 and the inner surface of the body part 520 and a space between a side surface of the opening/closing member 530 and the inner surface of the body part 520. Ultimately, the gas flows out to the external air entrance 135 through an inner space of the elastic member 540 (i.e., an inner space of the coil spring) and the opening of the cap part 550 (see FIG. 11). Therefore, the internal pressure of the gas-supplied space 116 is kept constant.

Since the cylinder 110, the injection piston 140, the gas-generating unit 130, the boss 137 and the pressure regulating valve 138 are the same as or similar to those disclosed in prior arts including Korean Patent No. 10-0507593 and may be easily applied to the present invention and configured by those skilled in the art, detailed descriptions of these elements will be omitted.

Hereinafter, the switch member 136 that is a main component of the internal pressure-adjustable liquid medicine injection apparatus 1000 according to the first embodiment of the present invention will be described with reference to FIGS. 1 to 9.

The switch member 136 is provided between the gas-supplied space 116 and the gas-generating space 139 to connect the gas-supplied space 116 to the atmosphere upon filling of the apparatus with the liquid medicine and to connect the gas-supplied space 116 to the gas-generating space 139 upon injection of the liquid medicine. To this end, the switch member 136 is provided among the atmosphere, the gas-supplied space 116 and the gas-generating space 139. Here, the term "connect" means that two or more spaces are connected to each other so as to allow a gas (air or carbon dioxide) to flow therebetween.

Here, the term "atmosphere" refers to the outside of the liquid medicine injection apparatus 1000 and is at atmospheric pressure. The atmosphere is not necessarily limited thereto but may be a place or an apparatus in which the atmospheric pressure or a similar pressure is kept or a pressure lower than the pressure in the liquid medicine storage space 114 upon injection of the liquid medicine is kept.

The switch member 136 will be described in detail with reference to FIGS. 1, 2, 6 and 9.

The switch member 136 includes a switch cylinder 310 and a switch piston 320.

The switch cylinder 310 is connected to the atmosphere, the gas-supplied space 116 and the gas-generating space 139. This switch cylinder 310 may be a cylindrical cylinder extending in one direction. Here, the switch cylinder 310 may extend in a radial direction of the cylinder 110. Naturally, the shape and/or extending direction of the cylinder are not limited thereto.

Figure 6:
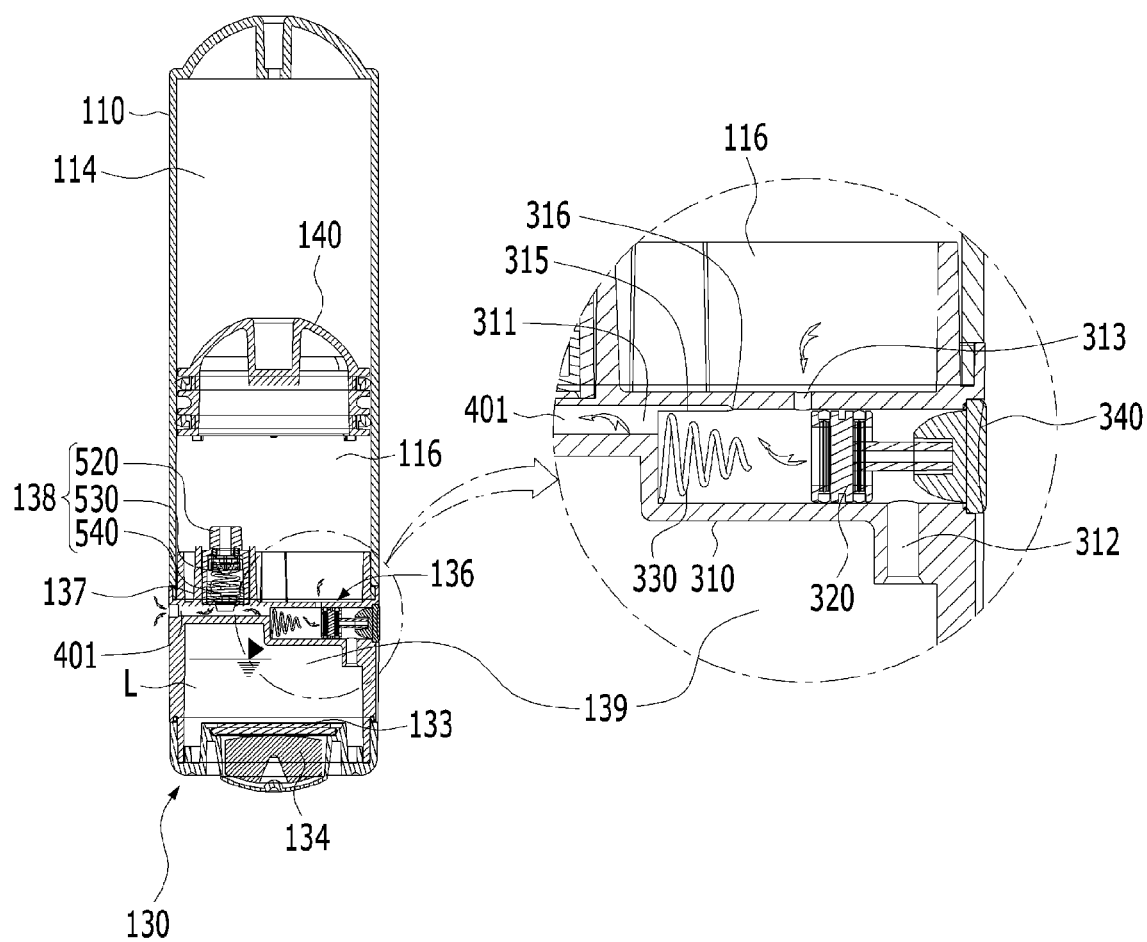
FIG. 6 shows a sectional view and an enlarged partial view of the internal pressure-adjustable liquid medicine injection apparatus 1000 according to the first embodiment of the present invention.
Figure 7:
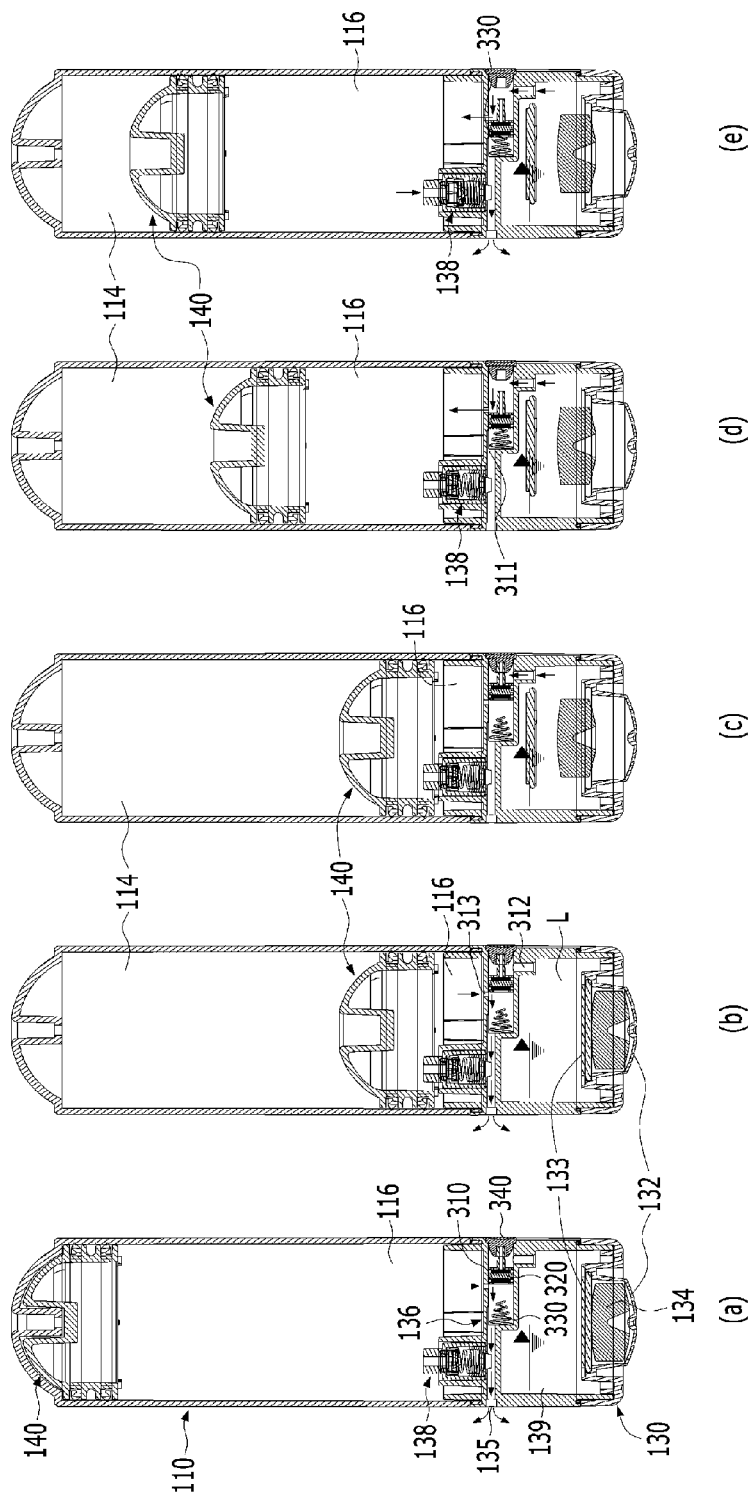
FIGS. 7($a$) to ($e$) are views illustrating an operational sequence of the internal pressure-adjustable liquid medicine injection apparatus 1000 according to the first embodiment of the present invention, showing a usage state where a pressure regulating valve is normally operated.
Figure 8:
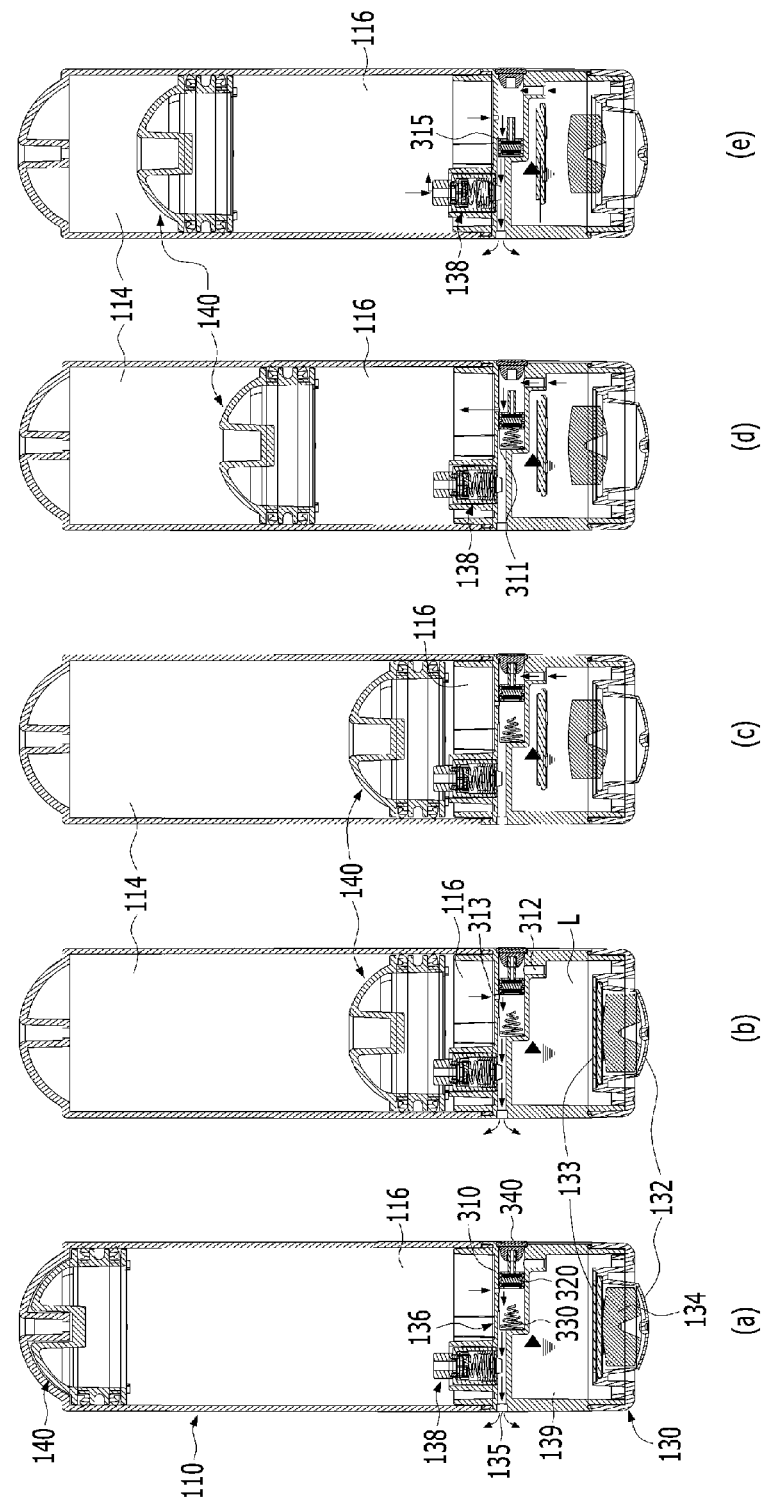
FIGS. 8($a$) to ($e$) are views illustrating an operational sequence of the internal pressure-adjustable liquid medicine injection apparatus 1000 according to the first embodiment of the present invention, showing a usage state where the pressure regulating valve is not normally operated.

Specifically, referring to FIG. 6, the switch cylinder 310 includes a first hole 311 connecting the atmosphere to the inside of the switch cylinder 310, a second hole 312 connecting the gas-generating space 139 to the inside of the switch cylinder 310, and a third hole 313 connecting the gas-supplied space 116 to the inside of the switch cylinder 310. The first hole 311, the second hole 312 and the third hole 313 serve as flow passages through which the gas flows.

At this time, the third hole 313 is placed between first hole 311 and the second hole 312. Moreover, with respect to a vertical direction (a longitudinal direction of the cylinder), the third hole 313 is formed closer to the first hole 311 than the second hole 312.

For example, the second hole 312 and the third hole 313 are formed in a sidewall of the switch cylinder 310, as shown in FIG. 6. The first hole 311 may be formed at any one of ends of the switch cylinder 310, as shown in FIG. 6. The third hole 313 is placed between the second hole 312 and the first hole 311. Furthermore, with respect to the vertical direction (the longitudinal direction of the cylinder), a distance between the first hole 311 and the third hole 313 is smaller than that between the first hole 311 and the second hole 312.

At this time, the other end of the switch cylinder 310 may be blocked. Alternatively, the switch cylinder 310 may further include a fourth hole 314. The fourth hole 314 is formed at a side opposite to the first hole 311, i.e., at the other end of the switch cylinder 310. The fourth hole 314 is blocked by a plug 340 to be described later. A detailed description of the plug 340 will be made later.

The aforementioned switch cylinder 310 may be formed integrally with the body part 131 of the gas-generating unit 130. Alternatively, the switch cylinder 310 may be separately manufactured and then coupled to the body part 131 of the gas-generating unit 130. Hereinafter, for the sake of simplicity of description, a case where the switch cylinder 310 is formed integrally with the body 131 part will be described, although the present invention is not limited thereto.

As shown in FIG. 6, the body part 131 of the gas-generating unit 130 has partition walls formed therein, and an external wall thereof has a generally cylindrical shape. The first hole 311, the second hole 312, the third hole 313 and the fourth hole 314 are formed in the internal partition walls or the external wall.

At this time, the body part 131 of the gas-generating unit 130 may include the external air entrance 135 connected to the switch cylinder 310. The external air entrance 135 is formed in a side surface of the body part 131 of the gas-generating unit 130 and is connected to the first hole 311 of the switch cylinder 310.

The external air entrance 135 may be provided with a gas permeable/liquid impermeable hydrophobic filter (not shown). This hydrophobic filter allows external air to flow into the apparatus through the external air entrance 135 but prevents water, a liquid medicine, a liquid contaminant and the like from flowing into the apparatus from the outside.

The body part 131 of the gas-generating unit 130 further includes an external air flow passage 401 connecting the external air entrance 135 to the first hole 311. The aforementioned pressure regulating valve 138 is connected to the external air flow passage 401 and is installed between the external air entrance 135 and the switch member 136.

The switch piston 320 is installed to be hermetically movable within the switch cylinder 310. To this end, the switch piston 320 includes ring-shaped protrusions formed around a body part thereof and sealing ring insertion grooves 321 placed between the respective protrusions. Sealing rings 323 are inserted into the sealing ring insertion grooves 321. The switch piston 320 can be hermetically moved within the switch cylinder 310 by these sealing rings 323 (see FIGS. 4 and 5).

Furthermore, the switch piston 320 connects the gas-supplied space 116 to the atmosphere or the gas-generating space 139 according to the position of the switch piston. In other words, the switch piston 320 connects the first hole 311 or the second hole 312 to the third hole 313.

For example, upon filling of the apparatus with the liquid medicine, the switch piston 320 connects the gas-supplied space 116 to the atmosphere and blocks the connection between the gas-supplied space 116 and the gas-generating space 139 (see FIGS. 6, 7(a) and 8(a)). That is, the switch piston 320 is positioned between the second hole 312 and the third hole 313 to connect the third hole 313 and the first hole 311 to each other. Accordingly, upon filling of the apparatus with the liquid medicine, the gas-supplied space 116 is connected to the atmosphere, so that the internal pressure thereof is equilibrated to the atmospheric pressure or is maintained at a slightly higher level than the atmospheric pressure.

Therefore, when an operation of filling the liquid medicine storage space 114 of the cylinder 110 with the liquid medicine is performed as preparation for injection of the liquid medicine into the patient's body, the injection piston 140, separating the liquid medicine storage space 114 from the gas-supplied space 116, can minimize its pushing action interrupting a flow of the liquid medicine introduced into the liquid medicine storage space 114, i.e., a liquid medicine inflow resistance, thereby facilitating the filling of the liquid medicine storage space with the liquid medicine.

Upon injection of the liquid medicine, the switch piston 320 connects the gas-supplied space 116 to the gas-generating space 139. In other words, the switch piston 320 is positioned between the first hole 311 and the third hole 313 to connect the second hole 312 and the third hole 313 to each other and block the connection between the atmosphere and the gas-supplied space 116. Accordingly, upon injection of the liquid medicine, the switch member 136 can guide the gas generated in the gas-generating unit 130 to the gas-supplied space 116.

In addition, the high pressure of the gas generated by the gas-generating unit 130 is exerted on the injection piston 140 in the gas-supplied space 116, so that the injection piston 140 can be efficiently moved forward and it is possible to stably and continuously inject the liquid medicine accommodated in the liquid medicine storage space 114 into the patient's body at a constant flow rate.

Meanwhile, referring to FIGS. 1 and 3 to 6, the switch member 136 may further include a plug 340.

The plug 340 blocks the fourth hole 314 of the switch cylinder 310 exposed to the outside as described above. For example, the switch cylinder 310 is placed within the body part 131 of the gas-generating unit 130 and includes the first hole 311 formed at one end thereof and the fourth hole 314 formed at the other end. At this time, the plug 340 clogs the fourth hole 314 to block the connection of the switch cylinder 310 to the outside via the fourth hole 314.

This plug 340 may receive a portion of a rod 322 of the switch piston 320 until a predetermined pressure is applied to the switch piston 320. Specifically, in order to stably fill the liquid medicine storage space with the liquid medicine, there is a need to cause the switch piston 320 to maintain the state where the gas-supplied space 116 is connected to the atmosphere upon filling of the liquid medicine storage space with the liquid medicine. At this time, since the plug 340 stably receives and holds the portion of the rod 322 of the switch piston 320, it is possible to stably connect the gas-supplied space 116 to the atmosphere upon filling of the liquid medicine storage space with the liquid medicine.

Figure 4:
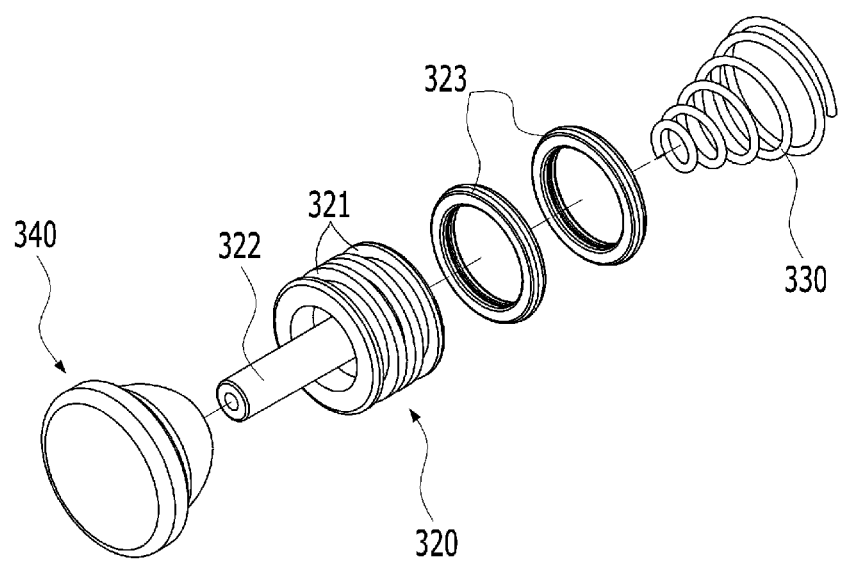
FIGS. 4 and 5 are an exploded perspective view and an exploded perspective sectional view schematically illustrating a disassembled state of a portion of the internal pressure-adjustable liquid medicine injection apparatus 1000 according to the first embodiment of the present invention, respectively.
Figure 5:
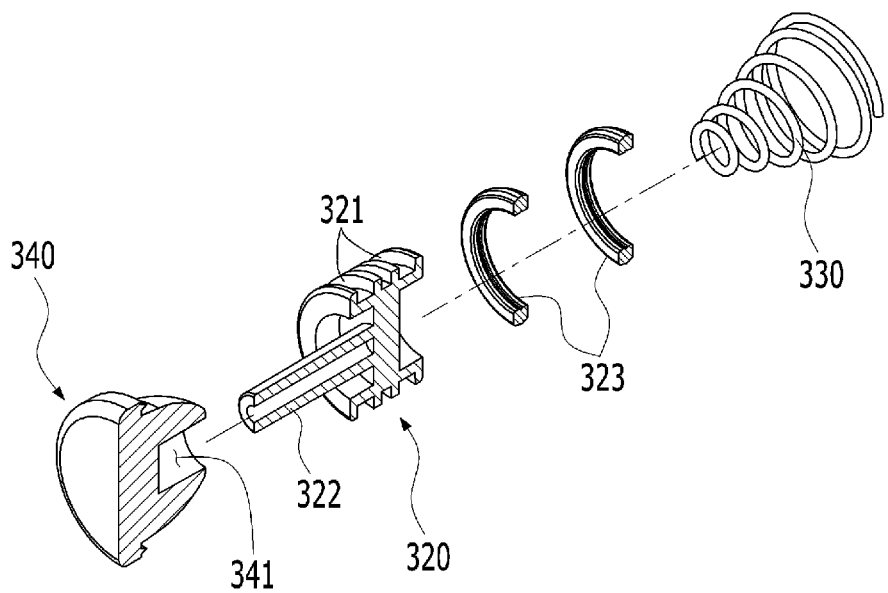

Referring to FIGS. 4 and 5, the plug 340 may have a generally hemispherical shape as shown in the figures to fit into the fourth hole 314.

Moreover, the plug 340 may include a coupling portion 341 facing toward an inside of the switch cylinder 310 (see FIGS. 5 and 6). For example, the coupling portion 341 is formed of a recess facing toward the inside of the switch cylinder 310, and the switch piston 320 includes the rod 322 guided by and received in the coupling portion 341. At this time, the rod 322 may include a hollow portion formed along a longitudinal direction thereof.

This plug 340 is preferably made of a light-transmitting material so that a user may visually recognize a movement of the switch piston 320 to understand whether the switch member 136 is normally operated. For example, the plug 340 may be made of a transparent material or a translucent material.

If a portion of the rod 322 of the switch piston 320 is still positioned on the plug 340 side even though the gas is generated in the gas-generating unit 130 upon injection of the liquid medicine, the user can recognize through the transparent plug 340 that the switch member 136 is not properly operated, and then take necessary measures.

Further, the switch piston 320 and/or a switch elastic member 330 to be described later are housed in the switch cylinder 310 through the fourth hole 314. The plug 340 seals the fourth hole 314 to prevent these elements from being detached from the switch cylinder 310.

Meanwhile, the switch member 136 can connect the gas-supplied space 116 to the atmosphere when the internal pressure of the gas-supplied space 116 exceeds an allowable value during the injection of the liquid medicine.

For example, if the aforementioned pressure regulating valve 138 fails or does not perform its function, the pressure in the gas-supplied space 116 may exceed the allowable value. In this case, the liquid medicine may be injected faster than an allowable rate, which may put a patient in danger.

As another example, there may be a case where the pressure regulating valve 138 is not present and the gas is excessively generated in the gas-generating unit 130 so that the pressure of the gas-supplied space 116 becomes higher. Even in this case, the liquid medicine may be injected faster than the allowable rate, which may put a patient in danger.

In order to prevent these cases, the switch member 136 may include a bypass flow passage 315 and the switch elastic member 330. Specifically, the switch cylinder 310 may include the bypass flow passage 315 therein.

The bypass flow passage 315 is connected to the first hole 311 and is formed along an inner wall of the switch cylinder 310. For example, the bypass flow passage 315 may take the shape of a groove connected to the first hole 311 and formed along the longitudinal direction of the switch cylinder 310. At this time, the bypass flow passage 315 is formed to extend from the first hole 311 and to be spaced apart from the third hole 313 by a predetermined distance.

Figure 9:
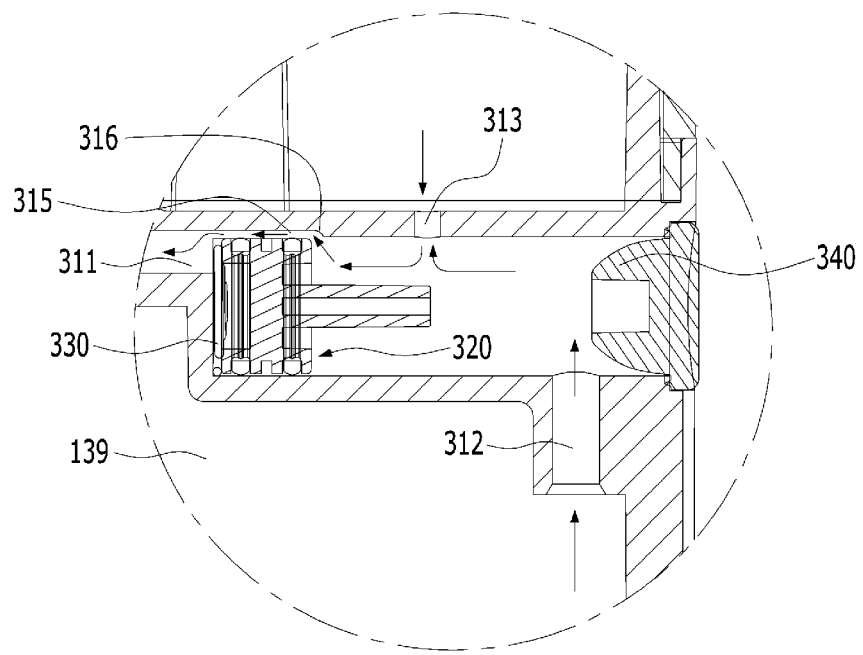
FIG. 9 is an enlarged view of FIG. 8($e$), illustrating that a switch member is operated as a preliminary (auxiliary) pressure regulating valve.

Referring to FIGS. 6 and 9, the bypass flow passage 315 is formed of a stepped portion 316. The stepped portion 316 is formed between the first hole 311 and the third hole 313.

When the bypass flow passage 315 will be described in terms of variations in an inner diameter of the switch cylinder 310, for example, it is assumed that an inner diameter of a portion of the switch cylinder 310 from the first hole 311 to the stepped portion 316 is "D1" and an inner diameter of a portion of the switch cylinder 310 from the stepped portion 316 to the third hole 313 is "D2." D1 is greater than D2 so that the stepped portion 316 may form the bypass flow passage 315. Therefore, the bypass flow passage 315 is formed as shown in FIGS. 6 and 9.

Furthermore, a distance from the first hole 311 to the stepped portion 316 may be smaller than a length of the switch elastic member 330. Alternatively, the distance from the first hole 311 to the stepped portion 316 may be smaller than the sum of the length of the switch elastic member 330 and a length of the switch piston 320. Here, the direction of the length may be parallel or substantially parallel to an axial direction of the switch cylinder 310.

Meanwhile, the switch elastic member 330 is installed within the switch cylinder 310 and is located between the atmosphere and the switch piston 320. The switch elastic member 330 can provide the switch piston 320 with an elastic force (i.e., a pushing elastic restoring force) to close the bypass flow passage 315 before the internal pressure of the gas-supplied space 116 exceeds the allowable value during the injection of the liquid medicine.

For example, the switch elastic member 330 is placed within the switch cylinder 310 and located between the first hole 311 and the switch piston 320. More specifically, the switch elastic member 330 may be disposed adjacent to the first hole 311 as shown in FIGS. 6 and 9. At this time, the switch elastic member 330 does not block the first hole 311.

Alternatively, the switch elastic member 330 may be located on the switch piston 320 side so as to be accommodated in a recess (see FIG. 5) formed in the switch piston 320.

In addition, the switch elastic member 330 is a coil spring and may be a conical coil spring as shown in the figures. However, the switch elastic member 330 is not limited thereto and various modifications such as a cylindrical coil spring may be made.

FIGS. 7(a) to (e) are views showing one usage state (a usage state where the pressure regulating valve is normally operated) of the liquid medicine injection apparatus according to the first embodiment of the present invention, in the order of operation.

Referring to FIG. 7(a), the injection piston 140 is in proximity to a front end of the cylinder 110, as a stage before the filling of the liquid medicine storage space with the liquid medicine or an initial stage of filling the liquid medicine storage space with the liquid medicine.

At this time, the switch member 136 connects the gas-supplied space 116 to the atmosphere. That is, the switch piston 320 is positioned between the second hole 312 and the third hole 313. Thus, the gas-supplied space 116 is connected to the atmosphere through the third hole 313, the inside of the switch cylinder 310, the first hole 311, the external air flow passage 401 and the external air entrance 135.

As the liquid medicine storage space is filled with the liquid medicine, the injection piston 140 is withdrawn rearward and the pressure in the gas-supplied space 116 is kept in an approximately equilibrium state with the atmosphere via the third hole 313, the inside of the switch cylinder 310, the first hole 311, the external air flow passage 401 and the external air entrance 135. At this time, the switch piston 320 is maintained in a state where a portion of the rod 322 thereof is accommodated in the plug 340. In other words, referring to FIG. 7(b), the switch member 136 is maintained in the state shown in FIG. 7(a) until the liquid medicine storage space is completely filled with the liquid medicine.

Accordingly, the pressure in the gas-supplied space 116 is stably equilibrated to the atmospheric pressure. In this state, when the operation of filling the liquid medicine storage space 114 with the liquid medicine is performed, the injection piston 140 can reduce its pushing action interrupting a flow of the liquid medicine flowing into the liquid medicine storage space 114, i.e., the liquid medicine inflow resistance, thereby facilitating the filling of the liquid medicine storage space with the liquid medicine.

Referring to FIGS. 7(c) and (d), when an external force is exerted on the cap part 132 after the filling of the liquid medicine storage space with the liquid medicine, the partition wall 133 is detached and the solid material 134 is fallen into the gas-generating space 139 in the body part 131. Then, the solid material reacts with the liquid material L to generate a gas, i.e., carbon dioxide.

The gas generated in the gas-generating space 139 flows into the switch cylinder 310 through the second hole 312 and pushes the switch piston 320, so that the switch piston 320 is moved and separated from the plug 340.

Thereafter, the introduced gas continuously moves the switch piston 320 along the switch cylinder 310. The second hole 312 and the third hole 313 are connected to each other by such movement of the switch piston 320 by a predetermined distance. In this state, the switch piston 320 is supported by the switch elastic member 330 so that the switch piston 320 is maintained in this state without further movement as long as the pressure is not remarkably increased (see FIG. 7(d)).

As the second hole 312 and the third hole 313 are connected to each other as described above, the gas flows into the gas-supplied space 116 and advances the injection piston 140 so as to inject the liquid medicine into the patient's body. During the injection of the liquid medicine, the switch piston 320 isolates the first hole 311 from the gas-generating space 139 and the gas-supplied space 116.

Referring to FIG. 7(e), the gas may be excessively generated during the injection of the liquid medicine to considerably increase the pressure in the gas-supplied space 116. As a result, the liquid medicine may be injected into the patient's body at a flow rate greater than a predetermined flow rate.

In order to avoid this situation, if the pressure in the gas-supplied space 116 is considerably increased, the pressure regulating valve 138 can be opened and the gas-supplied space 116 can be connected to the atmosphere to discharge the gas to the atmosphere. Therefore, as the pressure regulating valve 138 is opened, the pressure in the gas-supplied space 116 can be maintained to such an extent as to inject the liquid medicine.

Further, the pressure regulating valve 138 is closed when the pressure in the gas-supplied space 116 reaches an appropriate pressure as the gas flows out, so that the gas-supplied space 116 may be maintained at an appropriate pressure.

FIGS. 8(a) to (e) are views showing another usage state (a usage state where the pressure regulating valve is not normally operated) of the liquid medicine injection apparatus according to the first embodiment of the present invention, in the order of operation. Since operations shown in FIGS. 8(a) to (d) are the same as those described above with reference to FIGS. 7(a) to (d), descriptions thereof will be omitted. FIG. 8(e) shows that the switch member 136 serves as a preliminary (auxiliary) pressure regulating valve.

Referring to FIG. 8(e), during the injection of the liquid medicine, the gas may be excessively generated to considerably increase the pressure in the gas-supplied space 116. As a result, the liquid medicine may be injected into the patient's body at a flow rate greater than a predetermined flow rate.

At this time, the pressure regulating valve 138 may not be present or may fail or malfunction. In this case, when the internal pressure in the gas-supplied space 116 exceeds the allowable value during the injection of the liquid medicine, the switch member 136 connects the gas-supplied space 116 to the atmosphere.

Specifically, when the internal pressure in the gas-supplied space 116 exceeds the allowable value, the pressure in the switch cylinder 310 as well as the pressure in the gas-supplied space 116 are increased and the gas urges the switch piston 320 with a higher pressure. Accordingly, the switch elastic member 330 is compressed by the increased pressure of the gas, and the switch piston 320 is moved to a position where the bypass flow passage 315 is opened (see FIG. 9).

Accordingly, the gas that causes a pressure exceeding the pre-set pressure is discharged to the atmosphere through the bypass flow passage 315, the first hole 311, the external air flow passage 401 and the external air flow entrance 135. Therefore, the pressure in the gas-supplied space 116 can be maintained to such an extent as to inject the liquid medicine.

When the gas-supplied space 116 has an appropriate internal pressure as the gas flows out, the switch piston 320 is moved in a reverse direction by an elastic restoring force of the switch elastic member 330 to close the bypass flow passage 315 (at a position shown in FIG. 8(d)). With this operation, the switch member 136 can maintain the gas-supplied space 116 at an appropriate pressure.

With this operation, the liquid medicine injection apparatus according to the first embodiment of the present invention can provide a high liquid medicine injection pressure for steadily and continuously injecting the liquid medicine into the patient's body while being less influenced by a change in the environment such as an elevation of the apparatus, an external temperature or the like. Moreover, in order to solve a problem of difficulty in filling the liquid medicine storage space with the liquid medicine at a high liquid medicine injection pressure, the inside of the liquid medicine injection apparatus is caused to communicate with the external atmosphere upon filling of the liquid medicine storage space with the liquid medicine so as to equilibrate the internal pressure of the apparatus to the atmospheric pressure, thereby facilitating the filling of the liquid medicine storage space with the liquid medicine. Further, when the internal pressure of the apparatus exceeds the pre-set pressure due to the gas generated in the gas-generating unit, the switch member is operated as the pressure regulating valve so that the internal pressure of the apparatus may be kept constant at a pre-set pressure.

Hereinafter, a liquid medicine injection apparatus 1000' according to a second embodiment, which is a variation of the liquid medicine injection apparatus 1000 of the first embodiment of the present invention as described above, will be described. Meanwhile, prior to describing the second embodiment of the present invention, it should be noted that components that are the same as or similar to those of the aforementioned first embodiment are designated by like reference numerals and detailed descriptions of the components that are the same as or similar to those of the first embodiment will be partially omitted.

Figure 12:
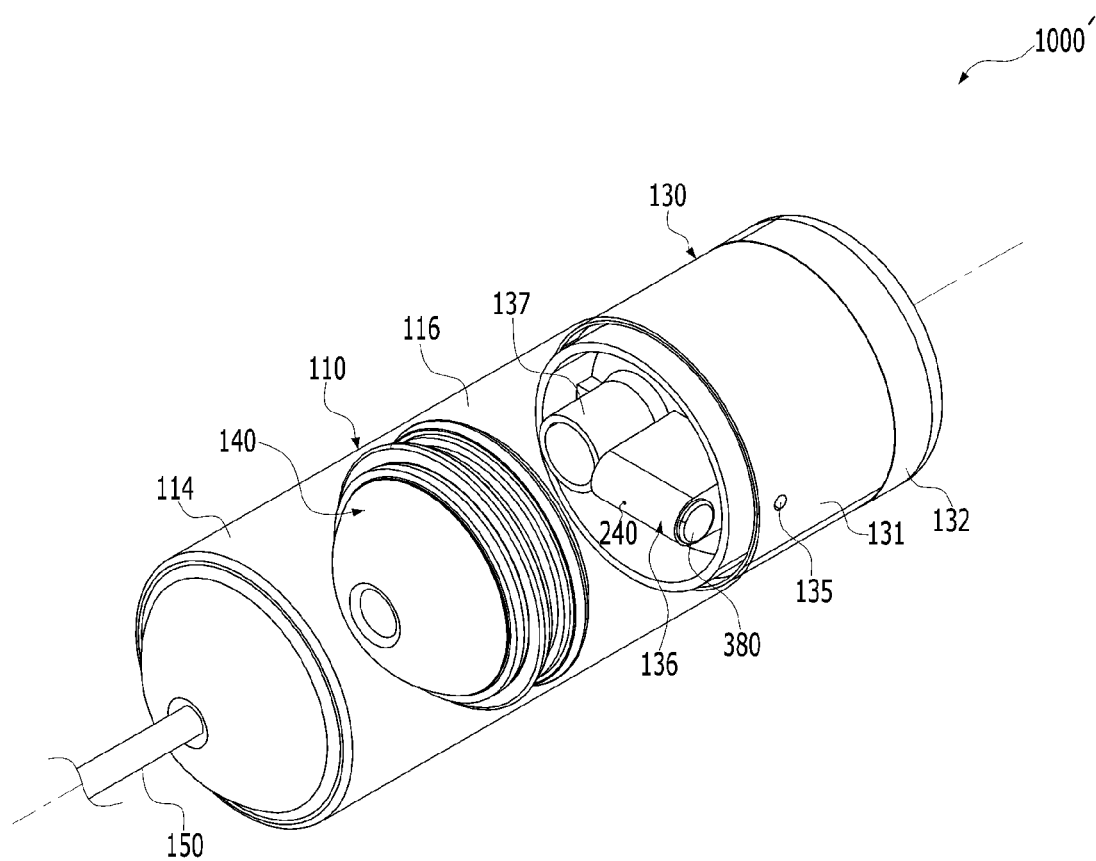
FIG. 12 is a perspective view showing an assembled state of an internal pressure-adjustable liquid medicine injection apparatus 1000' according to a second embodiment of the present invention.
Figure 13:
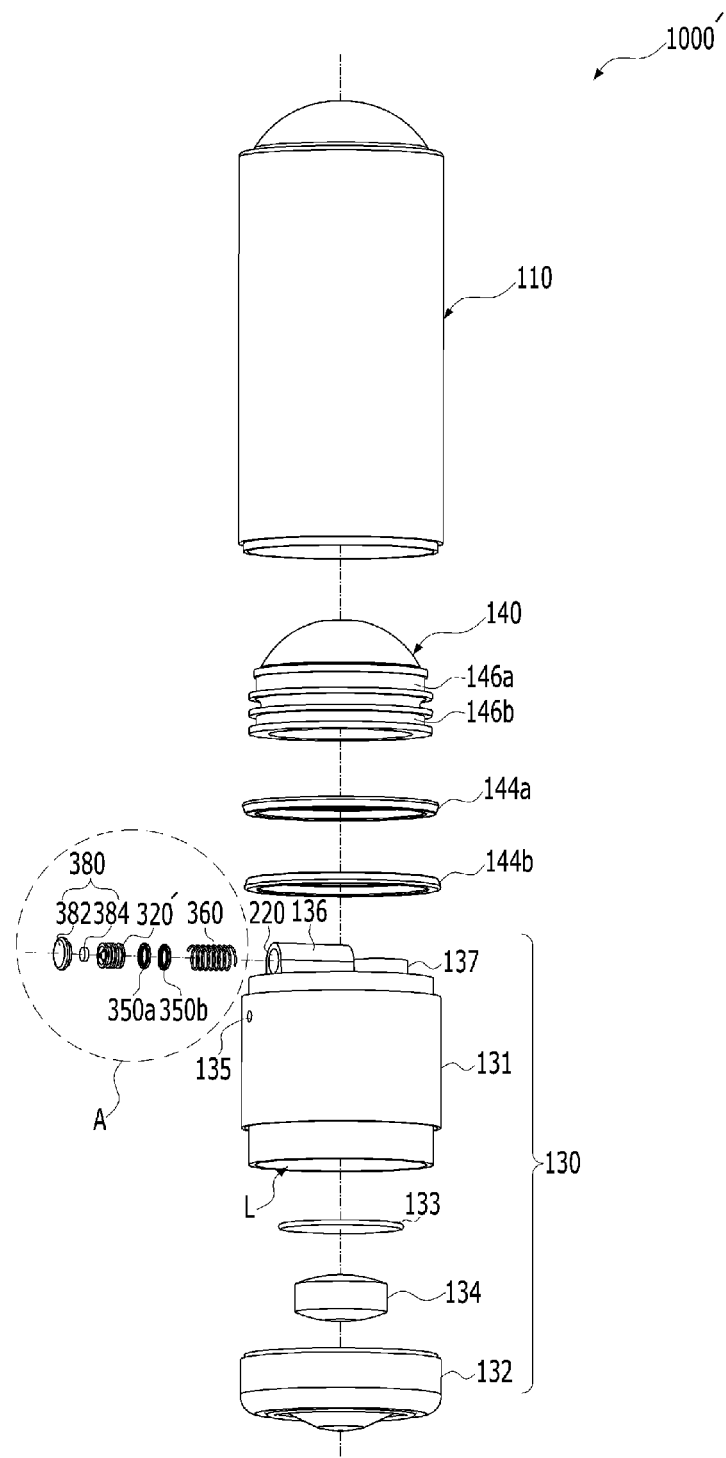
FIG. 13 is an exploded perspective view illustrating a disassembled state of the internal pressure-adjustable liquid medicine injection apparatus 1000' according to the second embodiment of the present invention.

As shown in FIGS. 12 and 13, the liquid medicine injection apparatus 1000' according to the second embodiment of the present invention, which can adjust an internal pressure depending on a liquid medicine filling mode and an injection mode, includes the generally cylindrical cylinder 110, the injection piston 140, the gas-generating unit 130 and the switch member 136 as main components. Meanwhile, since the cylinder 110, the injection piston 140, the gas-generating unit 130 and the boss 137 are disclosed in prior arts including Korean Patent No. 10-0507593 and can be easily applied to the present invention and configured by those skilled in the art, detailed descriptions of these elements will be omitted.

Hereinafter, the switch member 136 which is a main component of the internal pressure-adjustable liquid medicine injection apparatus 1000' according to the second embodiment of the present invention will be described with reference to FIGS. 12 to 17.

The switch member 136 is provided in the gas-generating unit 130 such that the switch member faces toward the inside of the gas-supplied space 116 of the cylinder 110 (see FIG. 12). This switch member 136 has an internal connection passage 220 for connecting the external air entrance 135 formed at one side of the body part 131 of the gas-generating unit 130 to the gas-supplied space 116, and a shut-off valve 320' which is hermetically moveable in the internal connection passage 220 and divides the internal connection passage 220 into an external air inflow space 222 into which external air can flow from the external air entrance 135, and a generated-gas inflow space 224 into which the gas from the gas-generating unit 130 flows. In addition, the external air entrance 135 is connected to the internal connection passage 220 through an air inflow passage 200 (see FIGS. 13, 16 and 17).

Figure 14:
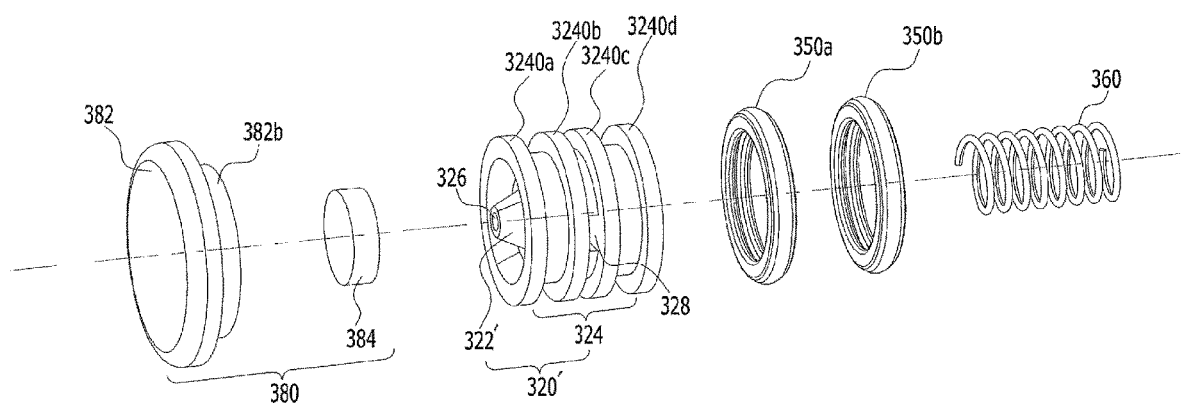
FIG. 14 is an enlarged view illustrating portion "A", i.e., a sealing member 380, a shut-off valve 320', sealing rings 350$a$ and 350$b$ and a tension spring 360 of the internal pressure-adjustable liquid medicine injection apparatus 1000' according to the second embodiment of the present invention shown in FIG. 13.
Figure 16:
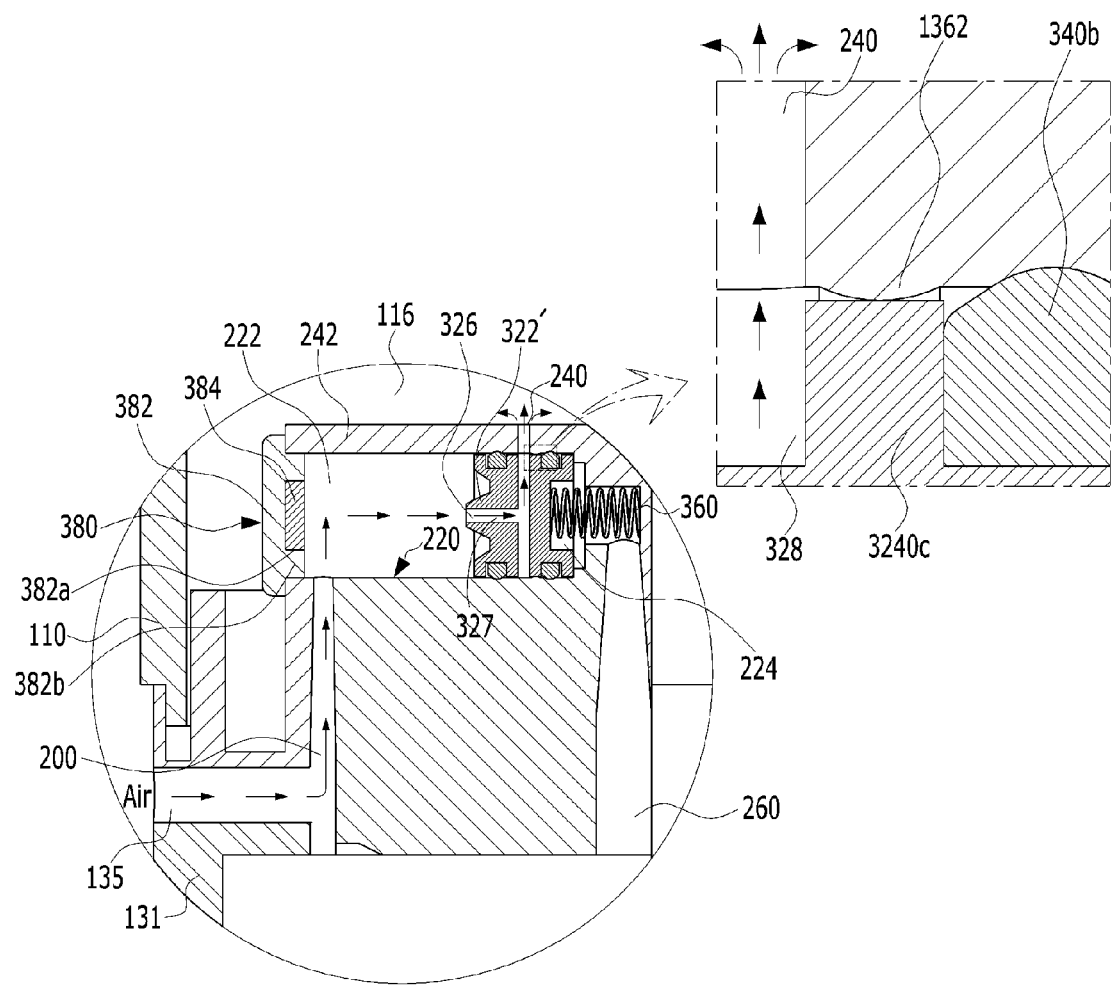
FIG. 16 is a view showing a usage state of the internal pressure-adjustable liquid medicine injection apparatus 1000' according to the second embodiment of the present invention, upon filling of the apparatus with a liquid medicine.

In the liquid medicine injection apparatus 1000' according to the second embodiment of the present invention, when the liquid medicine storage space is filled with the liquid medicine prior to the generation of the gas in the gas-generating unit 130, the shut-off valve 320' is positioned at a location where external air from the external air entrance 135 is caused to flow into the external air inflow space 222 and the external air inflow space 222 is in communication with the gas-supplied space 116, thereby equilibrating the internal pressure of the gas-supplied space 116 to the atmospheric pressure (see FIGS. 14 and 16). Therefore, when the operation of filling the liquid medicine storage space 114 of the cylinder 110 with the liquid medicine is performed as preparation for injection of the liquid medicine into the patient's body (see FIG. 12), the injection piston 140, separating the liquid medicine storage space 114 from the gas-supplied space 116, minimizes its pushing action interrupting a flow of the liquid medicine introduced into the liquid medicine storage space 114, i.e., a liquid medicine inflow resistance, thereby facilitating the filling of the liquid medicine storage space with the liquid medicine.

Figure 17:
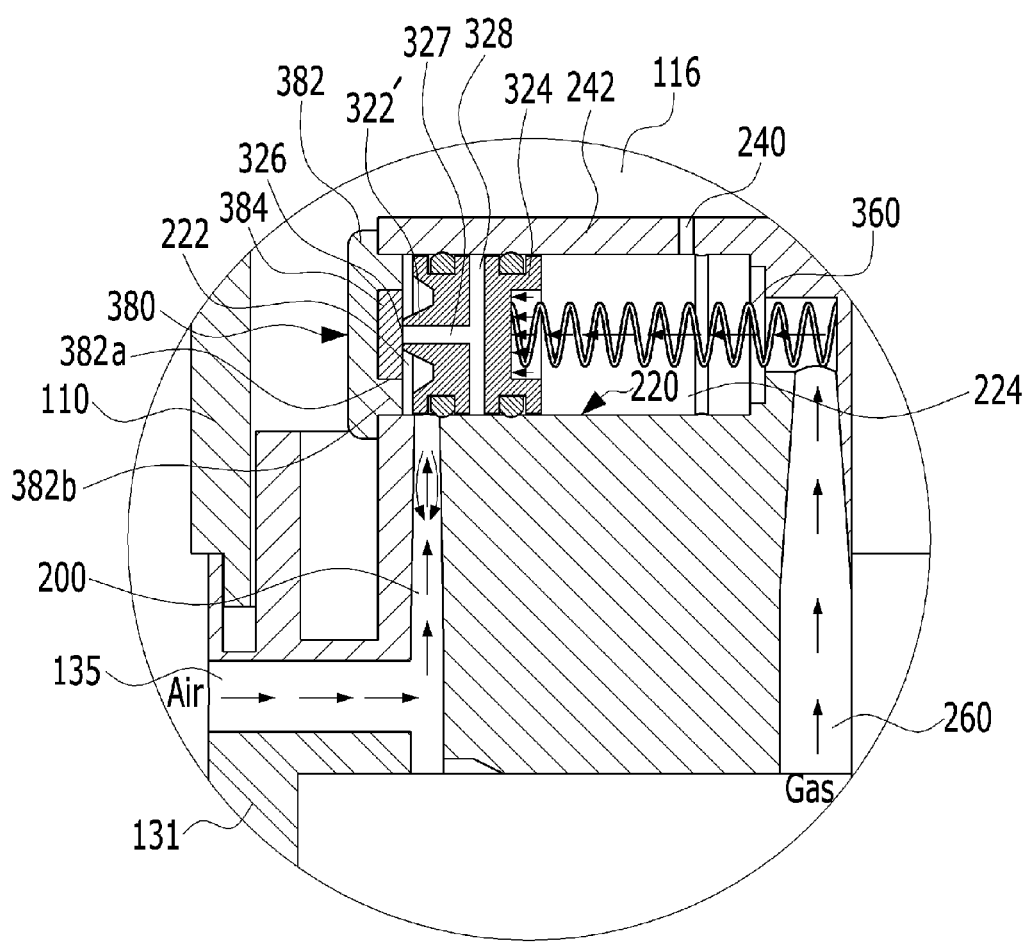
FIG. 17 is a view showing a usage state of the internal pressure-adjustable liquid medicine injection apparatus 1000' according to the second embodiment of the present invention, upon injection of the liquid medicine.

Meanwhile, in the liquid medicine injection apparatus 1000' according to the second embodiment of the present invention, when the liquid medicine is injected into the patient's body after the gas is generated in the gas-generating unit 130, the shut-off valve 320' is moved toward the external air inflow space 222 by a propulsive force of the gas flowing from the gas-generating unit 130 into the generated-gas inflow space 224, thereby blocking inflow of external air from the external air entrance 135 into the external air inflow space 222 (see FIGS. 14 and 17). Therefore, the high pressure of the gas generated by the gas-generating unit 130 is exerted on the injection piston 140 in the gas-supplied space 116 so that the injection piston 140 may be efficiently moved forward and the liquid medicine stored in the liquid medicine storage space 114 may be stably and continuously injected into the patient's body at a constant flow rate.

Figure 15:
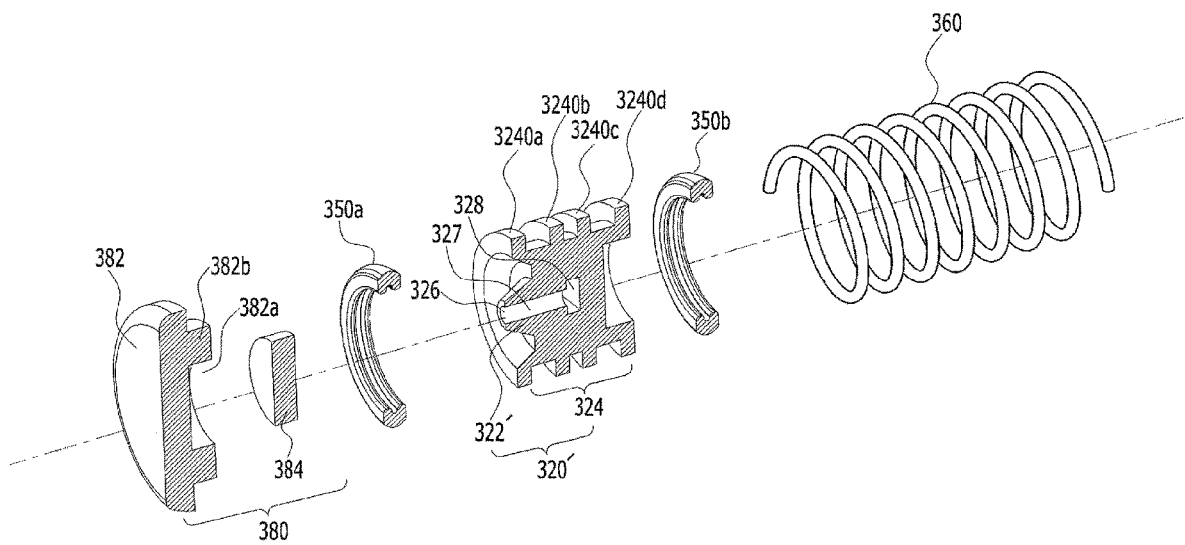
FIG. 15 is a longitudinal-sectional view illustrating the sealing member 380, a shut-off valve 320' and the sealing rings 350$a$ and 350$b$ shown in FIG. 14 (however, the tension spring 360 is shown in a perspective view for convenience of illustration and better understanding of the elements)

The shut-off valve 320' may have a front end 322' facing toward the external air inflow space 222, and a body part 324 hermetically movable along a guide wall 242 of the internal connection passage 220, and may be formed with a through passage 327 extending from a through hole 326 of the front end 322' to a through hole 328 formed in a side surface of the body part 324 (see FIGS. 15 and 16). A through hole 240 for communicating the internal connection passage 220 with the gas-supplied space 116 may be formed in the guide wall 242 of the internal connection passage 220 (see FIGS. 12 and 16).

When the liquid medicine storage space is filled with the liquid medicine before the gas is generated in the gas-generating unit, the through hole 328 formed in the side surface of the body part 324 of the shut-off valve is fixed at a position where the through hole 328 is aligned with the through hole 240 of the internal connection passage. Therefore, external air introduced into the external air inflow space 222 flows through the through hole 326 of the front end 322', the through passage 327 and the through hole 328 of the body part 324 of the shut-off valve, and flows into the gas-supplied space 116 through the through hole 240 of the internal connection passage, which is aligned with the through hole 328 of the body part 324 (see FIG. 16).

In this state, the internal pressure of the gas-supplied space 116 is equilibrated to the atmospheric pressure, and the liquid medicine inflow resistance caused by the injection piston 140, when the operation of filling the liquid medicine storage space 114 with the liquid medicine is performed, is reduced, thereby facilitating the filling of the liquid medicine storage space with the liquid medicine.

In addition, an end of the external air inflow space 222 of the internal connection passage 220 may be opened and a sealing member 380 may be further included to seal this opened end (see FIGS. 13 and 16). The sealing member 380 may be composed of a stepped sealing cap 382 and a rubber packing member 384 that is fitted into and coupled with a concave receiving portion 382*a* of such sealing cap (see FIGS. 15 and 16). A tension spring 360 and the shut-off valve 320' are sequentially housed in the internal connection passage 220 through the opened end (see FIGS. 13 and 16). A stepped portion 382*b* of the sealing cap is inserted into and tightly coupled with the opened end of the external air inflow space 222, and the rubber packing member 384 faces the external air inflow space 222.

When the liquid medicine is injected after the gas is generated in the gas-generating unit, the gas generated in the gas-generating unit flows into the generated-gas inflow space 224 through a gas-flowing passage 260, which connects the body part 131 of the gas-generating unit 130 and the generated-gas inflow space 224, so as to push a rear portion of the body part 324 of the shut-off valve 320'. The shut-off valve 320' is moved toward the external air inflow space 222 so that the front end 322' of the shut-off valve 320' is brought into contact with the sealing member 380 (see FIG. 17). This configuration prevents external air from the external air entrance 135 and the air inflow passage 200 from flowing into the through passage 327 of the shut-off valve 320' via the through hole 326 formed on the front end 322' of the shut-off valve 320'. In particular, when the front end 322' of the shut-off valve 320' presses and is in contact with the rubber packing member 384 constituting the sealing member 380, the front end 322' of the shut-off valve 320' is in close contact with the rubber packing member 384 and is blocked so that it is possible to reliably prevent external air from leaking via the through hole 326 formed on the front end 322' of the shut-off valve 320'. In this state, a high pressure of the gas generated by the gas-generating unit 130 is exerted on the injection piston 140, so that the injection piston 140 can be effectively moved forward and it is possible to stably and continuously inject the liquid medicine accommodated in the liquid medicine storage space 114 into the patient's body at a constant flow rate.

Moreover, a plurality of ring-shaped protrusions, preferably at least two, and more preferably four ring-shaped protrusions 3240*a*, 3240*b*, 3240*c* and 3240*d* may be formed on a circumference of the body part 324 of the shut-off valve 320' (See FIGS. 14 and 15). At least one protrusion 3240*c* of the ring-shaped protrusions is in close contact with a gentle stepped portion 1362 formed on the guide wall 242 of the internal connection passage 220 (see FIG. 16). Accordingly, before the gas generated in the gas-generating unit 130 is introduced into the generated-gas inflow space 224, it is possible to securely fix the shut-off valve 320 at a location where the through hole 328 formed in the side surface of the body part 324 of the shut-off valve 320' is aligned with the through hole 240 of the internal connection passage. Meanwhile, when the gas generated in the gas-generating unit 130 is introduced into the generated-gas inflow space 224, the pressure of the introduced gas is exerted on a rear portion of the body part 324 of the shut-off valve 320' so that the shut-off valve 320' may overcome an obstacle to a movement, which is caused by engagement of the ring-shaped protrusion 3240*c* with the stepped portion 1362, and be moved toward the external air inflow space 222 (see FIG. 17).

In other words, with the aforementioned configuration, it is possible to prevent the shut-off valve 320' from being moved due to temporary external impact or external air, so that the internal pressure of the gas-supplied space 116 is stably equilibrated to the atmospheric pressure before the gas is generated in the gas-generating unit, whereas upon generation of the gas in the gas-generating unit, the gas pressure generated in response to a liquid medicine injection mode enables the shut-off valve 320' to overcome an obstacle to a movement, which is caused by the stepped portion 1362, and to be moved toward the external air inflow space 222, and the front end 322' of the shut-off valve 320' is in close contact with the sealing member 380 to block the inflow of external air.

Further, each of sealing rings 350*a* or 350*b* can be inserted between the pair of two ring-shaped protrusions 3240*a* and 3240*b* or 3240*c* and 3240*d*. The sealing rings 350*a* and 350*b* allow the shut-off valve 320' to be hermetically moved along the guide wall 242 of the internal connection passage 220. In addition, the liquid medicine injection apparatus 1000' of the second embodiment of the present invention may further include the tension spring 360 fixedly installed in the generated-gas inflow space 224 and coupled to the body part 324 of the shut-off valve 320'.

When the gas is generated in the gas-generating unit, the gas pressure generated in response to the liquid medicine injection mode enables the shut-off valve 320' to overcome the elastic restoring force caused by the tension spring 360 and to be moved toward the external air inflow space 222, and the front end 322' of the shut-off valve 320' is in close contact with the sealing member 380 to block the inflow of external air (see FIG. 17). Moreover, the tension spring 360 prevents the shut-off valve 320' from being moved due to temporary external impact or external air by means of the elastic restoring force, thereby assisting in attaining a stable equilibrium between the internal pressure of the gas-supplied space 116 and the atmospheric pressure before the gas is generated in the gas-generating unit. In addition, when the generation of the gas is completed, the elastic restoring force of the tension spring helps to return the shut-off valve 320' to its original state where the injection of the liquid medicine is not initiated.

Further, the external air entrance 135 may be provided with a gas-permeable/liquid-impermeable hydrophobic filter (not shown). Such hydrophobic filter allows external air to flow into the apparatus through the external air entrance 135, but prevents water, a liquid medicine, a liquid contaminant and the like from flowing into the apparatus from the outside. As for the hydrophobic filter, those disclosed in prior arts or known in the art may be employed.

Meanwhile, most of the elements constituting the liquid medicine injection apparatus 1000' according to the second embodiment of the present invention which can adjust the internal pressure depending on the liquid medicine filling mode and the liquid medicine injection mode are formed of a material suitable for withstanding external impact and may be formed of a plastic material, a synthetic resin or the like that have been well known in the art. The sealing rings 350*a* and 350*b* and the rubber packing member 384 may be formed of a known elastic rubber material. Furthermore, plastic or spring steel may be used as a material for the tension spring 360. However, it will be readily understood by those skilled in the art that the present invention is not limited thereto and the aforementioned elements may be formed of various materials well known in the art, wherein the materials meet the object of the present invention, satisfy biocompatibility, are less corroded and have predetermined durability.

Hereinafter, operations of the liquid medicine injection apparatus 1000' according to the second embodiment of the present invention, which is configured as such and can adjust the internal pressure depending on the liquid medicine filling mode and the liquid medicine injection mode, will be described with reference to FIGS. 16 and 17 while focusing on the switch member 136.

(A) Operation of Filling the Liquid Medicine Storage Space with the Liquid Medicine Before Generation of a Gas: See FIG. 16

When the liquid medicine storage space is filled with the liquid medicine before generation of the gas in the gas-generating unit, the through hole 328 formed in the side surface of the body part 324 of the shut-off valve 320' is aligned with the through hole 240 of the internal connection passage. In this state, the shut-off valve 320' is fixed with respect to the internal connection passage 220.

For example, at least one protrusion 3240c of the four ring-shaped protrusions 3240a, 3240b, 3240c and 3240d is in close contact with the gentle stepped portion 1362 formed in the guide wall 242 of the internal connection passage 220. Therefore, when the liquid medicine storage space is filled with the liquid medicine before generation of the gas in the gas-generating unit, it is possible to reliably prevent the shut-off valve 320' from being moved due to temporary external impact or external air.

In other words, the shut-off valve 320' is fixed at a location where external air from the external air entrance 135 flows into the external air inflow space 222 and the external air inflow space 222 is in communication with the gas-supplied space 116.

External air flows from the external air entrance 135 into the external air inflow space 222 via the air inflow passage 200. Then, the external air introduced into the external air inflow space 222 flows through the through hole 326 of the front end 322', the through passage 327, and the through hole 328 of the body part 324 of the shut-off valve 320', and then flows into the gas-supplied space 116 through the through hole 240 of the internal connection passage aligned with the through hole 328 of the body part 324.

Accordingly, the internal pressure of the gas-supplied space 116 is stably equilibrated to the atmospheric pressure. In addition, the tension spring 360 prevents the shut-off valve 320' from being moved due to temporary external impact or external air by means of its elastic restoring force, so that the tension spring helps the internal pressure of the gas-supplied space 116 to be stably equilibrated to the atmospheric pressure. In this state, when the operation of filling the liquid medicine storage space 114 with the liquid medicine is performed, the injection piston 140 can reduce its pushing action interrupting a flow of the liquid medicine introduced into the liquid medicine storage space 114, i.e., the liquid medicine inflow resistance, thereby facilitating the filling of the liquid medicine storage space with the liquid medicine.

(B) Operation of Injecting the Liquid Medicine after Generation of the Gas: See FIG. 17

When the liquid medicine is injected after generation of the gas in the gas-generating unit, the gas generated in the gas-generating unit flows into the generated-gas inflow space 224 through the gas-flowing passage 260 that connects the body part 131 of the gas-generating unit 130 and the generated-gas inflow space 224 to each other.

A propulsive force of the introduced gas pushes a rear portion of the body part 324 of the shut-off valve 320' to overcome an obstacle to a movement, which is caused by engagement of the ring-shaped protrusion 3240c with the stepped portion 1362. Further, the gas pressure pushing the rear portion of the body part 324 of the shut-off valve 320' also overcomes the elastic restoring force of the tension spring 360. Accordingly, the shut-off valve 320' is guided along the guide wall 242 of the internal connection passage 220 and is moved toward the external air inflow space 222.

Then, the shut-off valve 320' is moved toward the external air inflow space 222 so that the front end 322' of the shut-off valve 320' is brought into contact with the sealing member 380. In particular, when the front end 322' of the shut-off valve 320' presses against and is brought into contact with the rubber packing member 384 constituting the sealing member 380, the front end 322' of the shut-off valve 320' is in close contact with and blocked by the rubber packing member 384, so that it is possible to reliably prevent external air from leaking to the through hole 326 formed at the front end 322' of the shut-off valve 320'.

In this state, an inflow of external air from the external air entrance 135 and the air inflow passage 200 into the through passage 327 of the shut-off valve 320' via the through hole 326 formed at the front end 322' of the shut-off valve 320' is blocked. In other words, external air cannot flow through the through hole 326 of the front end 322', the through passage 327 and the through hole 328 of the body part 324 of the shut-off valve 320' so that external air also cannot flow into the gas-supplied space 116 through the through hole 240 of the internal connection passage.

Therefore, the high pressure of the gas generated by the gas-generating unit 130 is exerted on the injection piston 140 in the gas-supplied space 116, so that the injection piston 140 can be effectively moved forward and the liquid medicine filled in the liquid medicine storage space 114 can be stably and continuously injected into the patient's body at a constant flow rate.

In other words, with operations (A) and (B) described above, the liquid medicine injection apparatus according to the second embodiment of the present invention can provide a high liquid medicine injection pressure suitable for steady and continuous injection of the liquid medicine into the patient's body while being less influenced by changes in the environment such as an elevation, an external temperature or the like. Moreover, in order to solve the problem of difficulty in filling the liquid medicine storage space with the liquid medicine at a high liquid medicine injection pressure, the liquid medicine injection apparatus according to the second embodiment allows the inside of the apparatus to communicate with the external atmosphere so as to equilibrate the internal pressure of the apparatus to the atmospheric pressure upon filling of the liquid medicine storage space with the liquid medicine, thereby facilitating the filling of the liquid medicine storage space with the liquid medicine.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. An internal pressure-adjustable liquid medicine injection apparatus comprising:
   a cylinder having one end with a liquid medicine-flowing tube connected thereto and the other end with a gas-generating unit coupled thereto, wherein a liquid medicine flows into and out of the cylinder through the liquid medicine-flowing tube and the gas-generating unit has a gas-generating space in which a gas is generated;

an injection piston hermetically movable in the cylinder and dividing an internal space of the cylinder into a liquid medicine storage space and a gas-supplied space, wherein the liquid medicine flows through the liquid medicine-flowing tube and fills the liquid medicine storage space and the gas generated in the gas-generating unit is supplied to the gas-supplied space; and a switch member provided between the gas-supplied space and the gas-generating space to connect the gas-supplied space to an atmosphere upon filling of the liquid medicine storage space with the liquid medicine and to connect the gas-supplied space to the gas-generating space upon injection of the liquid medicine, wherein the switch member is installed in the gas-generating unit to face toward the inside of the gas-supplied space;

the switch member has an internal connection passage for connecting an external air entrance formed at one side of the gas-generating unit to the gas-supplied space, and a shut-off valve, the shut-off valve being hermetically moveable in the internal connection passage and dividing the internal connection passage into an external air inflow space configured to allow external air to flow from the external air entrance, and a generated-gas inflow space into which the gas from the gas-generating unit flows;

when the liquid medicine storage space is filled with the liquid medicine prior to the generation of the gas in the gas-generating unit, the shut-off valve is positioned at a location where the external air entrance is in communication with the external air inflow space and the external air inflow space is in communication with the gas-supplied space, and the connection between the gas-supplied space and the generated-gas inflow space is blocked, thereby equilibrating the internal pressure of the gas-supplied space to an atmospheric pressure; and when the liquid medicine is injected after the gas is generated in the gas-generating unit, the gas generated in the gas-generating unit flows into the generated-gas inflow space to move the shut-off valve toward the external air inflow space, thereby blocking inflow of the external air from the external air entrance into the external air inflow space and connecting the gas-supplied space to the generated-gas inflow space so that a pressure of the gas generated by the gas-generating unit is exerted on the injection piston in the gas-supplied space.

2. The internal pressure-adjustable liquid medicine injection apparatus of claim 1, wherein the shut-off valve has a front end facing the external air inflow space, and a body part hermetically movable along a guide wall of the internal connection passage, and is formed with a through passage extending a through hole of the front end to a through hole formed in a side surface of the body part.

3. The internal pressure-adjustable liquid medicine injection apparatus of claim 2, wherein the guide wall of the internal connection passage is formed with a through hole for communicating the internal connection passage with the gas-supplied space.

4. The internal pressure-adjustable liquid medicine injection apparatus of claim 3, wherein when the liquid medicine storage space is filled with the liquid medicine prior to the generation of the gas in the gas-generating unit, the through hole formed in the side surface of the body part of the shut-off valve is placed a location where the through hole formed in the side surface is aligned with the through hole of the internal connection passage, and wherein the external air inflow space is in communication with the gas-supplied space via the through hole of the front end, the through passage, the through hole formed in the side surface of the body part, and the through hole of the internal connection passage.

5. The internal pressure-adjustable liquid medicine injection apparatus of claim 2, wherein a plurality of ring-shaped protrusions are formed on a circumference of the body part of the shut-off valve, and at least one of the ring-shaped protrusions is in close contact with at least one stepped portion formed on the guide wall of the internal connection passage.

6. The internal pressure-adjustable liquid medicine injection apparatus of claim 5, wherein a sealing ring is inserted between and coupled to the ring-shaped protrusions.

7. The internal pressure-adjustable liquid medicine injection apparatus of claim 1, wherein an end of the external air inflow space of the internal connection passage is opened, and the apparatus further comprises a sealing member to seal the end.

8. The internal pressure-adjustable liquid medicine injection apparatus of claim 7, wherein the sealing member comprises a stepped sealing cap and a rubber packing member fitted into and coupled with a concave receiving portion of the sealing cap, a stepped portion of the sealing cap is inserted into and tightly coupled with the end of the external air inflow space, and the rubber packing member faces the external air inflow space.

9. The internal pressure-adjustable liquid medicine injection apparatus of claim 8, wherein the front end of the shut-off valve presses against and is brought into contact with the rubber packing member constituting the sealing member, and the front end of the shut-off valve is in close contact with and blocked by the rubber packing member.

10. The internal pressure-adjustable liquid medicine injection apparatus of claim 7, wherein when the liquid medicine is injected after the gas is generated in the gas-generating unit, the gas generated in the gas-generating unit flows into the generated-gas inflow space through a gas-flowing passage for connecting the gas-generating unit to the generated-gas inflow space, so as to push a rear portion of the body part of the shut-off valve; and the shut-off valve is moved toward the external air inflow space so that the front end of the shut-off valve is brought into contact with the sealing member, thereby preventing the external air from the external air entrance from flowing via the through hole of the front end of the shut-off valve.

11. The internal pressure-adjustable liquid medicine injection apparatus of claim 7, further comprising a tension spring fixedly provided in the generated-gas inflow space and coupled with the body part of the shut-off valve.

12. The internal pressure-adjustable liquid medicine injection apparatus of claim 11, wherein the tension spring and the shut-off valve are housed in the internal connection passage through the end of the external air inflow space.

13. The internal pressure-adjustable liquid medicine injection apparatus of claim 1, wherein a gas-permeable/liquid-impermeable hydrophobic filter is provided at the external air entrance.

14. An internal pressure-adjustable liquid medicine injection apparatus comprising:

a cylinder having one end with a liquid medicine-flowing tube connected thereto and the other end with a gas-generating unit coupled thereto, wherein a liquid medicine flows into and out of the cylinder through the liquid medicine-flowing tube and the gas-generating unit has a gas-generating space in which a gas is generated;

an injection piston hermetically movable in the cylinder and dividing an internal space of the cylinder into a liquid medicine storage space and a gas-supplied space, wherein the liquid medicine flows through the liquid medicine-flowing tube and fills the liquid medicine storage space and the gas generated in the gas-generating unit is supplied to the gas-supplied space; and a switch member provided between the gas-supplied space and the gas-generating space to connect the gas-supplied space to an atmosphere upon filling of the liquid medicine storage space with the liquid medicine and to connect the gas-supplied space to the gas-generating space upon injection of the liquid medicine, wherein the switch member comprises:
a switch cylinder connected to the atmosphere, the gas-supplied space and the gas-generating space; and
a switch piston movably installed in the switch cylinder to connect the gas-supplied space to the atmosphere or connect the gas-supplied space to the gas-generating space depending on a location of the switch piston within the switch cylinder;

wherein the switch cylinder comprises:
a first hole connecting the atmosphere to the inside of the switch cylinder;
a second hole connecting the gas-generating space and the inside of the switch cylinder; and
a third hole connecting the gas-supplied space and the inside of the switch cylinder and positioned between the first hole and the second hole;

wherein upon filling of the liquid medicine storage space with the liquid medicine, the switch piston is positioned between the third hole and the second hole in the switch cylinder to connect the gas-supplied space to the atmosphere and to block the connection between the gas-supplied space and the gas-generating space; and upon injection of the liquid medicine, the switch piston is positioned between the third hole and the first hole in the switch cylinder to connect the gas-supplied space and the gas-generating space and to block the connection between the atmosphere and the gas-supplied space.

15. The internal pressure-adjustable liquid medicine injection apparatus of claim 14, wherein the switch cylinder further comprises a fourth hole exposed to an outside and the switch member further comprises a plug for blocking the fourth hole.

16. The internal pressure-adjustable liquid medicine injection apparatus of claim 15, wherein the plug is made of a light-transmitting material so that a user may visually recognize a movement of the switch piston to understand whether the switch member is normally operated.

17. The internal pressure-adjustable liquid medicine injection apparatus of claim 16, wherein the plug is made of a transparent material or a translucent material.

18. The internal pressure-adjustable liquid medicine injection apparatus of claim 14, wherein upon injection of the liquid medicine, if the internal pressure of the gas-supplied space exceeds a preset pressure value, the switch member discharges an amount of gas corresponding to an excess pressure to an outside through a bypass flow passage for connecting the gas-supplied space to the atmosphere.

19. An internal pressure-adjustable liquid medicine injection apparatus comprising:
a cylinder having one end with a liquid medicine-flowing tube connected thereto and the other end with a gas-generating unit coupled thereto, wherein a liquid medicine flows into and out of the cylinder through the liquid medicine-flowing tube and the gas-generating unit has a gas-generating space in which a gas is generated;

an injection piston hermetically movable in the cylinder and dividing an internal space of the cylinder into a liquid medicine storage space and a gas-supplied space, wherein the liquid medicine flows through the liquid medicine-flowing tube and fills the liquid medicine storage space and the gas generated in the gas-generating unit is supplied to the gas-supplied space; and a switch member provided between the gas-supplied space and the gas-generating space to connect the gas-supplied space to an atmosphere upon filling of the liquid medicine storage space with the liquid medicine and to connect the gas-supplied space to the gas-generating space upon injection of the liquid medicine, wherein the switch member comprises:
a switch cylinder connected to the atmosphere, the gas-supplied space and the gas-generating space and comprising a bypass flow passage for connecting the gas-supplied space to the atmosphere;
a switch piston movably installed in the switch cylinder to connect the gas-supplied space to the atmosphere or connect the gas-supplied space to the gas-generating space depending on a location of the switch piston within the switch cylinder; and
a switch elastic member provided in the switch cylinder, positioned between the atmosphere and the switch piston, and capable of exerting an elastic force on the switch piston so as to close the bypass flow passage before the internal pressure of the gas-supplied space exceeds a preset pressure value during the injection of the liquid medicine;

wherein the switch cylinder comprises:
a first hole connecting the atmosphere to the inside of the switch cylinder;
a second hole connecting the gas-generating space and the inside of the switch cylinder;
a third hole connecting the gas-supplied space and the inside of the switch cylinder and positioned between the first hole and the second hole; and wherein if the internal pressure of the gas-supplied space exceeds a preset pressure value, the bypass flow passage connects the gas-supplied space to the atmosphere, the bypass flow passage being connected to the first hole and being formed along an inner wall of the switch cylinder, and taking the shape of a groove connected to the first hole and formed along the longitudinal direction of the switch cylinder.

20. The internal pressure-adjustable liquid medicine injection apparatus of claim 19, wherein the switch cylinder further comprises:
a stepped portion formed between the first hole and the third hole and forming the bypass flow passage connected to the first hole.

21. The internal pressure-adjustable liquid medicine injection apparatus of claim 20,
wherein upon filling of the liquid medicine storage space with the liquid medicine, the switch piston is positioned between the third hole and the second hole in the switch cylinder to connect the gas-supplied space to the atmosphere;

wherein upon injection of the liquid medicine, the switch piston is positioned between the third hole and the stepped portion in the switch cylinder to connect the gas-supplied space to the gas-generating space; and wherein if the internal pressure of the gas-supplied space exceeds a preset pressure value during the injection of the liquid medicine, the switch piston is positioned between the first hole and the stepped portion in the switch cylinder to open the bypass flow passage for connecting the gas-supplied space to the atmosphere.

22. The internal pressure-adjustable liquid medicine injection apparatus of claim 20, wherein a distance from the first hole to the stepped portion is smaller than a sum of a length of the switch elastic member and a length of the switch piston, or smaller than the length of the switch elastic member.

* * * * *